(12) United States Patent
Markovsky et al.

(10) Patent No.: US 10,274,489 B2
(45) Date of Patent: Apr. 30, 2019

(54) ASSESSING ASSAY ANALYSIS DEVELOPMENT

(71) Applicant: Charm Sciences, Inc., Lawrence, MA (US)

(72) Inventors: Robert J. Markovsky, Brentwood, NH (US); Richard T. Skiffington, North Reading, MA (US); Stanley E. Charm, Boston, MA (US)

(73) Assignee: Charm Sciences, Inc., Lawrence, MA (US)

( * ) Notice: Subject to any disclaimer, the term of this patent is extended or adjusted under 35 U.S.C. 154(b) by 485 days.

(21) Appl. No.: 14/823,321

(22) PCT Filed: Feb. 11, 2014

(86) PCT No.: PCT/US2014/015794
§ 371 (c)(1),
(2) Date: Oct. 18, 2016

(87) PCT Pub. No.: WO2014/126918
PCT Pub. Date: Aug. 21, 2014

(65) Prior Publication Data
US 2017/0184585 A1    Jun. 29, 2017

Related U.S. Application Data

(60) Provisional application No. 61/790,600, filed on Mar. 15, 2013, provisional application No. 61/763,688, filed on Feb. 12, 2013.

(51) Int. Cl.
*G01N 21/84* (2006.01)
*B01L 3/00* (2006.01)
(Continued)

(52) U.S. Cl.
CPC .......... *G01N 33/558* (2013.01); *B01L 3/5023* (2013.01); *G01N 21/8483* (2013.01);
(Continued)

(58) Field of Classification Search
CPC ......... B01L 2300/023; B01L 2300/027; B01L 2300/0654; B01L 2300/069;
(Continued)

(56) References Cited

U.S. PATENT DOCUMENTS

| 5,985,675 A | 11/1999 | Charm et al. ................. 436/514 |
| 6,124,585 A | 9/2000 | Riedel et al. .............. 250/208.1 |

(Continued)

FOREIGN PATENT DOCUMENTS

WO    WO 2012027583    3/2012

*Primary Examiner* — Jennifer Wecker
(74) *Attorney, Agent, or Firm* — MacCord Mason PLLC

(57) ABSTRACT

Assessing test results development during assay analysis is shown and described. In one embodiment, an apparatus generates an assessment of diagnostic test development from an assay. The apparatus may include an optical detector aligned in an optical path with the assay. Further, the optical detector may perform continuous image detection of the assay to generate an assessment testing development. In some examples, the assessment is a graphical display of diagnostic development. In yet other embodiments, a method of assessing diagnostic test development may include signaling the optical detector to perform continuing image detection of the assay and generating an assessment of said diagnostic test development. The assessment may include graphing a reflectance detected on the assay on a display board.

20 Claims, 19 Drawing Sheets

(51) Int. Cl.
*G01N 33/558* (2006.01)
*G01N 33/543* (2006.01)

(52) U.S. Cl.
CPC .. *G01N 33/54366* (2013.01); *B01L 2300/023* (2013.01); *B01L 2300/027* (2013.01); *B01L 2300/069* (2013.01); *B01L 2300/0654* (2013.01); *B01L 2300/0825* (2013.01); *B01L 2400/0406* (2013.01)

(58) Field of Classification Search
CPC ..... B01L 2300/0825; B01L 2400/0406; B01L 3/5023; G01N 21/8483; G01N 33/54366; G01N 33/558
See application file for complete search history.

(56) References Cited

U.S. PATENT DOCUMENTS

| | | |
|---|---|---|
| 6,319,466 B1 | 11/2001 | Markovsky et al. ........... 422/56 |
| 6,475,805 B1 | 11/2002 | Charm et al. ................. 436/514 |
| 7,097,983 B2 | 8/2006 | Markovsky et al. .......... 435/7.1 |
| 7,317,532 B2 | 1/2008 | Sharrock et al. ............. 356/436 |
| 7,410,808 B1 | 8/2008 | Saul et al. .................... 436/514 |
| 7,499,170 B2 | 3/2009 | Sasaki et al. ................. 356/436 |
| 7,785,899 B2 | 8/2010 | Saul et al. .................... 436/518 |
| 9,360,478 B2 | 6/2016 | Abbott et al. ................ 73/53.01 |
| 9,970,923 B2 | 5/2018 | Sturman et al. .................. 21/17 |
| 2003/0207442 A1* | 11/2003 | Markovsky .............. A23D 9/00 435/287.2 |
| 2005/0036148 A1 | 2/2005 | Phelan .......................... 356/446 |
| 2005/0227370 A1* | 10/2005 | Ramel ...................... C12Q 1/00 436/514 |
| 2008/0019887 A1* | 1/2008 | Lohmann ............... G01N 21/05 422/243 |
| 2010/0009430 A1* | 1/2010 | Wan .................. B01L 3/502746 435/287.1 |
| 2010/0156273 A1 | 6/2010 | Utsunomiya et al. ........ 313/498 |
| 2011/0275162 A1* | 11/2011 | Xie ........................ G01N 21/78 436/164 |
| 2011/0318755 A1 | 12/2011 | Piasio et al. ................... 435/7.9 |
| 2013/0157381 A1* | 6/2013 | Pang ................. B01L 3/502715 436/501 |
| 2013/0230844 A1* | 9/2013 | Egan ................... G01N 21/6486 435/5 |

* cited by examiner

ASSESSING ASSAY ANALYSIS DEVELOPMENT

This application claims the benefit to PCT application to PCT/US14/015794, filed Feb. 11, 2014; U.S. provisional application Nos. 61/763,688, filed Feb. 12, 2013, and 61/790,600, filed Mar. 15, 2013, all of which are incorporated herein by reference in their entireties.

FIELD OF THE TECHNOLOGY

The present disclosure relates generally to analytical testing, and more particularly to improved assessment of assay analysis development during the detection of an analyte.

BACKGROUND

Reagent strips and films are often a helpful analytical tool in the fields of clinical chemistry, analytical medicine and food sanitation diagnostics. For example, it is advantageous to determine or to test, through quantitative or qualitative methods, various matrices, including body fluids such as serum and urine, and food, such as meat products, fruit, vegetables, milk, honey and the like. Such matrices can be tested for a variety of analytes including a variety of chemicals, biochemicals and biological molecules such as bacteria, antibiotics, for example, sulfa drugs, tetracyclines, beta-lactam drugs; toxins, such as aflatoxin, zearalonone, ochratoxin, T-2, and vomitoxin, pesticides such as organo-phosphates and carbamates, and active metabolites, either in materials or on the surface of materials or a combination thereof.

Generally, lateral flow assays are membrane-based test devices in which a sample that is suspected of containing the analyte of interest is placed at or near one end of the membrane strip. The sample is carried to the opposite end of the membrane strip by a mobile phase that traverses the membrane strip, for example by capillary action. While traversing the membrane strip, the analyte in the test sample, if any, encounters one or more reagents. The reagents can include binders for the analyte. Binders can be mobile and, therefore, flow with the sample, or be immobilized on the test strip as a capture agent. Depending on the test configuration, either the analyte binder, the analyte itself, or some other reagent in the test system will be captured by the immobilized capture agent and, thereby, produce a detectable signal. The signal can be generated by a label provided within the assay. The detectable signal can be measured, such as by an optical reader.

The presence and, in some cases, the concentration, of an analyte on a reagent strip may be determined by measuring the optical reflectance from an area of development on the strip. For example, the area of development on the strip may be an area of color development. Percent reflectance can be used to determine the result.

Testing commonly occurs in a controlled environment, such as a laboratory, but testing in non-laboratory settings is also common. In some applications speed and ease of use is particularly important. For example, in food processing it would be advantageous for tests to be run in non-laboratory settings because processors must wait for results. Further, it would also be advantageous for tests to be run on trucks during transport of the items. For that reason, it would be advantageous to accelerate the speed of testing, reduce the cost of equipment and tests, improve the ruggedness of the apparatus, and enhance the ease of use and simplicity of operation. In addition, it is advantageous to have confidence that test results are valid. Therefore, systems, methods and devices herein also assist in preventing fraudulent use of pre-run, known negative assays in place of true samples or use of assays pre-marked to provide a negative result that does not reflect the true nature of the sample. It is also desirable to increase the ruggedness of the assays, systems and test procedures.

Therefore, Applicants desire systems and methods for analyte detection without the drawbacks presented by traditional lateral flow assay systems and methods.

SUMMARY

This disclosure provides improved analyte detection that is convenient, efficient, and safe for the user, particularly when used to simplify test operation, enhance test development assessment, improve test reliability, improve test ruggedness, improve testing speed, reduce the possibility of mistakes, reduce the chances of incorrect results from dirt/debris contamination, and reduce the options for trickery and mistake by limiting operator (human) interaction and/or dynamically assessing assay, including test strip, development during testing. This disclosure further provides improved assessment of assay analysis development during the detection of an analyte. For example, the apparatus may be adapted to perform a continuous image detection of the assay that includes displaying the image sensing data in graphical form. The graphical than may be displayed to the user on a display board, for instance illustrating real-time image sensing test results. In particular examples, image sensing can be frequent, for example in intervals of about fifteen seconds, or less.

In one embodiment, a lateral flow assay system to generate a diagnostic test development from an assay includes an incubator, a reader, and a user interface having a graphical display. In some examples, the graphical display includes a first axis having a measurement of reflectance on the assay. Further, the graphical display may include a second axis having a measurement of a remission value of the assay. Typically, the reflectance measurement and the remission value define, i.e. graphically illustrate, the diagnostic test development. The incubator is generally adapted to incubate the lateral flow assay. The reader is generally adapted to read the diagnostic test development on the assay currently as the incubator incubates the assay.

In another embodiment, a lateral flow assay system to generate a diagnostic test development from an assay includes an incubator, a reader, and a user interface. Again, the incubator may be adapted to incubate the assay in a variety of configurations. The reader may be similar adapted to read a variety of diagnostic test developments on the assay currently as the incubator incubates the assay. The user interface may have a graphical display of the diagnostic test development.

In other embodiments, an assay measurement apparatus to generate a diagnostic test development from an assay includes an optical detector and a microprocessor to generate an assessment of the diagnostic development. The optical detector may be aligned in an optical path with the assay, wherein the optical detector may be adapted to acquire an image detection on the assay. The microprocessor may be in communication with the optical detector, wherein the microprocessor may be adapted to signal the optical detector to perform continuous image detection of the assay to generate an assessment of said diagnostic development. The assessment may be a graphical display of said diagnostic development. The graphical display may include an assessment about every fifteen seconds. Other embodiments include assessments of less than about every fifteen seconds. Further, the assessment may include a lowest reflectance point on the assay. The apparatus may include a user interface. For instance, the user interface may have an integrated circuit board that supports a display board. Typically, the user interface is adapted to view the graphical display of the diagnostic development. The assay may be a lateral flow assay. For example, the assay may be a lateral, capillary-flow, elongated test strip.

In another embodiment, a method of assessing diagnostic test development from an assay includes aligning an optical detector in an optical path with the assay, acquiring an image detection on the assay, signaling the optical detector to perform continuing image detection of the assay, and generating a graphical assessment of the continuing image detection of the diagnostic test development. The generating of the assessment may include graphing a reflectance detected from the assay on a display board In yet other embodiments, an assay measurement apparatus to generate a diagnostic test result from an assay includes an optical detector and a microprocessor. The optical detector may be aligned in an optical path with said assay. The optical detector may be adapted to acquire an image detection on said assay due to an aberration on said assay. The microprocessor may be in communication with said optical detector. The microprocessor may be adapted to signal said optical detector to perform continuous image detection of said assay to generate said diagnostic test result.

The optical detector may comprise a decoding sensor that is adapted to align with said assay and decode a reference coding on said assay. The reference coding may activate a corresponding diagnostic test in said optical detector. The apparatus may include a multichannel reader and said reference coding may activate a corresponding channel in said multichannel reader. The apparatus may include an incubator and said reference coding may activate a corresponding incubation temperature.

The decoding sensor may be a color sensor. The color sensor may be a photodiode with sensitivity to wavelengths chosen from red, blue, green and a combination thereof. The decoding sensor may be an RFID reader. The decoding sensor may be a bar code reader.

In one example, the apparatus includes a light source. The light source may be an array of discrete light sources. For instance, the discrete light sources may comprise one light emitting diode and/or multiple light emitting diodes. The light emitting diodes may be colored diodes chosen from red, green, blue and a combination thereof. The light source may comprise an illumination profile suitable for reflecting on a test strip assay. The light source may be aligned with a light aperture, exposing light from said light source on said assay. A first mirror may be below said light aperture. A focusing lens may receive light from said first mirror. A second mirror may be positioned to direct light from said focusing lens to said optical detector. A lighting processor may be adapted to trigger said light source to emit light for a desired pattern. The lighting processor may include data storage for said desired light-emission pattern.

In another example, the optical detector will not generate a test result until said decoding sensor decodes said reference coding. The optical detector may be a light-to-voltage sensor. The optical detector may comprise a photodiode in said optical path with said assay coupled to an integrated circuit. The integrated circuit may be a monolithic integrated circuit. The optical detector may include an amplifier. The amplifier may be a translucence amplifier.

The apparatus may include a memory adapted to store information corresponding to an imaging parameter for said image detection. The decoding sensor may be chosen from a color sensor, a RFID reader, a bar code reader and a combination thereof. The optical detector may include an optical window that is adapted to block debris from contact with said optical detector. The optical detector may include an optics housing to enclose said optical detector and that is adapted to block debris from contact with said optical detector. The optical detector may monitor a diagnostic test progress. The optical detector may monitor a pre-test parameter prior to generating a diagnostic test result. The optical detector may monitor at least one pre-test parameter after said optical detector has acquired at least one image detection on said assay.

In another embodiment, in an assay measurement apparatus having an imaging detector and a microprocessor, a memory that is in communication with said microprocessor and is adapted to store information corresponding to an imaging parameter. The memory may include an instruction for monitoring a pre-test analysis on said assay. The memory may include an instruction for generating a diagnostic test result on said assay. The pre-test parameter may include a theoretical reflectance value.

In one example, the assay may include at least one test line and at least one control line, and whereby said theoretical reflectance value is a comparison between a reflectance value at said test line and a reflectance value at said control line. A reflectance value on said assay that is inconsistent with said theoretical reflectance value may indicate an inadequate flow on said assay. The inadequate flow may trigger a detectable signal to generate a no-result response. The reflectance value on said assay that is inconsistent with said theoretical reflectance value may indicate a prior analyte development on said assay. The reflectance values may suggest prior analyte development may trigger a detectable signal to deactivate said assay measurement apparatus. The reflectance value on said assay that is inconsistent with said theoretical reflectance value may indicate a contaminated optical path.

The contaminated optical path may trigger a detectable signal to generate a no-result response. The instruction for generating a test result may correspond to an image detection on said assay. The image detection may be an optical reflectance value or a transmission value. The assay may include at least one test line and at least one control line, and whereby said optical reflectance value is a comparison between a reflectance value at said test line and a reflectance value at said control line. The apparatus may be adapted to perform a continuous image detection of said assay. In some examples, the apparatus may be adapted to perform a continuous image detection of said assay that includes displaying the image sensing data in graphical form that is displayed to the user. Image sensing can be frequent, for example intervals of 15 seconds or less. The assay may be a lateral flow assay. The assay may also be a lateral, capillary-flow, elongated test strip.

The test result may be determined within about thirty seconds of optical detector activation. The test result may be determined within about sixty seconds of optical detector activation. More rapid test results are possible with continuous sensing. Such results may occur in less than about sixty seconds, depending on the time required. When continuous and frequent image sensing occurs faster results may be also possible, for example with strong positives and/or absolute negative samples. The apparatus may include a power source. The power source may be a vehicle battery. Further, the optical detector may be in communication with an onboard vehicle system.

In other embodiments, an assay measurement apparatus to generate a test result from an assay may include an imaging detector and a microprocessor with an associated memory in communication with said microprocessor. The imaging detector may be adapted to decode a reference coding on said assay and to acquire an image detection on said assay due to an aberration on said assay. The microprocessor may be adapted to signal said imaging detector to generate said test result. The memory may be in communication with said microprocessor and may be adapted to store information corresponding to a plurality of imaging parameters. The memory may include a parameter for monitoring a pre-test analysis on said assay. The memory may include a parameter for generating said diagnostic test result from said assay.

A reference coding may activate a corresponding diagnostic test in said optical detector. A multichannel reader and said reference coding may activate a corresponding channel in said multichannel reader. The apparatus may include an incubator and said reference coding may activate a corresponding incubation temperature.

The imaging detector may be adapted to decode said test reference coding and comprise a decoding sensor. The decoding sensor may be a color sensor. The color sensor may be a photodiode with sensitivity to wavelengths chosen from red, blue, green and a combination thereof. The decoding sensor may be an RFID reader. The decoding sensor may also be a bar code reader.

Typically, the apparatus includes a light source. The light source may be an array of discrete light sources. The discrete light sources may comprise light emitting diodes. The light emitting diodes may be colored diodes chosen from red, green, blue and a combination thereof. The light source may comprise an illumination profile suitable for reflecting on a test strip assay. The light source may be aligned with a light aperture exposing said light source on said assay. The light source may include a first mirror below said light aperture. A focusing lens may receive light from said first mirror. A second mirror may be positioned to direct light from said focusing lens to said optical detector. A lighting processor may be adapted to trigger said light source to emit light for a desired pattern. The lighting processor may include data storage for said desired light-emission pattern. The optical detector may not generate a test result, or even initiate reading of the test, until said decoding sensor decodes said reference coding.

The optical detector may be a light-to-voltage sensor. The optical detector may comprise a photodiode coupled to an integrated circuit in said optical path with said assay. The integrated circuit may be a monolithic integrated circuit. The optical detector may include an amplifier. The amplifier may be a translucence amplifier. The optical detector may include an optical window that is adapted to block debris from contact with said optical detector. The optical detector may also include an optics housing to enclose said optical detector and that is adapted to block debris from contact with said optical detector.

In some examples, the optical detector may monitor a diagnostic test progress. The optical detector may monitor a pre-test parameter prior to generating a diagnostic test result. Further, the optical detector may monitor at least one pre-test parameter after said optical detector has acquired at least one image detection on said assay. The pre-test parameter may include a theoretical reflectance value. The assay may include at least one test line and at least one control line, and whereby said theoretical reflectance value is a comparison between a reflectance value at said test line and a reflectance value at said control line. Theoretical reflectance values may also be a pre-set preset parameter value for the control line or the test line. For instance, the control line may be the theoretical reflectance value. A reflectance value on said assay that is inconsistent with said theoretical reflectance value may indicate an inadequate flow on said assay. The inadequate flow may trigger a detectable signal to generate a no-result response. Further, a reflectance value on said assay that is inconsistent with said theoretical reflectance value may indicate a prior analyte development on said assay. The prior analyte development may trigger a detectable signal to generate a no-result response. Yet further, a reflectance value on said assay that is inconsistent with said theoretical reflectance value may indicate a contaminated optical path. The contaminated optical path may trigger a detectable signal to get a no-result response reading, and/or deactivate said assay measurement apparatus.

An instruction for generating a test result may correspond to an image detection on said assay. The image detection may be an optical reflectance value. The assay may include at least one test line and at least one control line, and whereby said optical reflectance value is a comparison between a reflectance value at said test line and a reflectance value at said control line. The apparatus may be adapted to perform a continuous image detection of said assay. The assay may be a lateral flow assay. For instance, the assay may be a lateral, capillary-flow, elongated test strip. Further, the apparatus may include a means for a power source.

In yet another embodiment, a lateral flow assay for the detection of an analyte and having a test zone and a control zone, a surface having a reflectance profile includes at least one flow reference and at least one test result reference. The at least one flow reference area may be adapted to enable monitoring of a pre-flow development along said assay. The at least one test result reference area may be adapted to enable monitoring a pre-test detection of said analyte on said assay.

The reflectance profile may include a theoretical light reflectance measurement. The theoretical light reflectance measurement may comprise a no-flow development theoretical value. The no-flow development value may be a reflectance value of about 85. A reflectance value of greater than about 85 may generate a signal to deactivate said detection of said analyte. The flow reference area may include at least one downstream flow reference line. The downstream flow reference line may include a theoretical reflectance value after said flow reference line receives reagent flow thereon. The flow reference area may include both an intermediary flow reference line and a downstream flow reference line. The intermediary flow reference line may include a theoretical reflectance value after said flow reference line receives reagent flow thereon. The theoretical light reflectance measurement may comprise a no-analyte pre-test development theoretical value. The flow reference may also be the control zone.

The test result reference area may include at least one test line having a theoretical reflectance value. The test result reference area may include at least one control line having a theoretical reflectance value. The test result reference area may include at least one test line having a theoretical reflectance value and at least one control line having a theoretical reflectance value. A pre-set difference between said at least one test line's theoretical reflectance value and said at least one control line's theoretical reflectance value may activate a test result. Further, a pre-set difference between said at least one test line's theoretical reflectance value and said at least one control line's theoretical reflectance value may trigger an error. The error may withhold a test result.

In other embodiments, a lateral, capillary-flow elongated test strip includes a test zone, a control zone and a surface having a reflectance profile. The lateral, capillary-flow elongated test strip may have at least one reagent for the detection of at least one analyte in a sample. The test zone may include immobilized thereon a test zone capture agent that is adapted for capturing said at least one reagent. The control zone may include at least one control zone capture agent having a different binding affinity for said at least one reagent. The reflectance profile may be adapted to enable monitoring of said test strip continuously until the detection of said analyte. Typically, the test strip generates a detectable signal for detecting said analyte in said sample. In some examples, inadequate control line development, for instance according to reflectance and/or transmission at the control line, may trigger an error. In these examples, the error may trigger a signal to generate a no-result response.

The test strip may comprise a coding system having at least one reference code with a corresponding testing sequence. The testing sequence may include at least one temperature adjustment parameter. Further, the testing sequence may include an optical reader test parameter. The optical reader test parameter may include a reader channel selection. The reader test parameter may include an associated feature chosen from a standard curve, a does-response curve and a combination thereof. The reader test parameter may include at least one associated positive control point and at least one associated negative control point. The coding system may include a color matrices. The color matrices may include a color chosen from red, blue, green and combination thereof. The color matrices may be associated with a corresponding diagnostic test. The coding system may include a bar code. The coding system may include an RFID tag.

The test strip may include a first end having a sample absorbing material. The test strip may include a peel strip to introduce sample onto the sample absorbing material. The peel strip may include a peel tab at one end of the peel strip to facilitate movement of said peel strip. The sample absorbing material may be adapted to receive about 0.1 to about 1.0 mL of a fluid. The sample absorbing material may comprise a dry cellulosic material. Further, the test strip may include an opposed second end having a reactor detector material. The test strip may include a releasing area having a mobile phase receptor for the at least one analyte. The test strip may be sized and adapted to be enclosed within a test strip cavity. Further, the test strip may be sized and adapted to be enclosed within a test strip cavity of a removable incubation module. Typically, the test strip is adapted for selecting the detection of a diagnostic test group chosen from an antibiotic analyte, toxic analyte, analyte class, a combination thereof and the like.

The test zone may include at least one analyte reference line having a theoretical reflectance value. The theoretical reflectance value may be associated with a flow parameter on said test strip. The test zone surface may include a first analyte reference line having a first theoretical reflectance value and a second analyte reference line having a second theoretical reflectance value. The control zone surface may include at least one control line having a theoretical reflectance value. For instance, the theoretical reflectance value may be an optical reflectance value. The control zone may include a first control line having a first theoretical reflectance value and a second control line having a second theoretical reflectance value. In some examples, the reflectance profile is adapted to enable monitoring of said test strip prior to the detection of said analyte. Further, the test result may be detected within about thirty to about sixty seconds.

In yet another embodiment, a lateral, capillary-flow elongated test strip includes a test zone including immobilized thereon a test zone capture agent adapted for capturing at least one binder, a control zone including at least one control zone capture agent having a different binding affinity for said at least one binder, a surface having a reflectance profile adapted to enable monitoring of said test strip and a coding system having at least one coding signal, for instance a coding to correspond to a testing sequence to characterize said test strip. The reflectance profile may include at least one flow reference area adapted to enable monitoring of a flow development along said assay, and at least one monitor reference area adapted to enable monitoring of detection of said analyte on said assay.

The testing sequence may include at least one temperature adjustment parameter. The testing sequence may include an optical reader test parameter. The optical reader test parameter may include a reader channel selection. The optical reader test parameter may include an associated feature chosen from a standard curve, a does-response curve and a combination thereof. Further, the optical reader test parameter may include at least one associated positive control point and at least one associated negative control point. The coding system may include a color matrix. The color matrices may be associated with a corresponding diagnostic test. The coding system may include a bar code. The coding system may include an RFID tag.

In some examples, the test strip may include a first end having a sample absorbing material. The test strip may include a peel strip to introduce sample onto the sample absorbing material. The peel strip may include a peel tab at one end of the peel strip to facilitate movement of said peel strip. The sample absorbing material may be adapted to receive about 0.1 to about 1.0 mL of a fluid. The sample absorbing material may comprise a dry cellulosic material. The test strip may include an opposed second end having a reactor detector material. The test strip may include a releasing area having a mobile phase receptor for the at least one analyte. The test strip may be sized and adapted to be enclosed within a test strip cavity. Further, the test strip may be sized and adapted to be enclosed within a test strip cavity of a removable incubation module. Typically, the test strip is adapted for selecting the detection of a diagnostic test group chosen from an antibiotic analyte, toxic analyte, analyte class, a combination thereof and the like, either quantitatively, qualitatively or both.

The test zone may include at least one analyte reference line having a theoretical reflectance value. Typically, the theoretical reflectance value is associated with a flow parameter on said test strip. The test zone may include a first analyte reference line having a first theoretical reflectance value and a second analyte reference line having a second theoretical reflectance value. The control zone may include at least one control line having a theoretical reflectance value. The theoretical reflectance value may be an optical reflectance value. A control zone may include a first control line having a first theoretical reflectance value and a second control line having a second theoretical reflectance value. The theoretical light reflectance measurement may comprise a no-flow development theoretical value. The no-flow development value may be a reflectance value of about 85. The reflectance value of greater than about 85 may generate a signal to deactivate said detection of said analyte.

In other examples, the flow reference area may include at least one downstream flow reference line. The downstream flow reference line may include a theoretical reflectance value after said flow reference line receives reagent flow thereon. The flow reference area may include an intermediary flow reference line and a downstream flow reference line. The intermediary flow reference line may include a theoretical reflectance value after said flow reference line receives reagent flow thereon. The theoretical light reflectance measurement may comprise a no-analyte pre-test development theoretical value. The test result reference area may include at least one test line having a theoretical reflectance value. The test result reference area may include at least one control line having a theoretical reflectance value. The test result reference area may include at least one test line having a theoretical reflectance value and at least one control line having a theoretical reflectance value. A pre-set difference between said at least one test line's theoretical reflectance value and said at least one control line's theoretical reflectance value may activate a test result. Further, a pre-set difference between said at least one test line's theoretical reflectance value and said at least one control line's theoretical reflectance value may trigger an error. Typically, the error withholds a test result, including generating a no-result response.

In yet another embodiment, in an assay system having an incubator and a reader to generate a test result from an assay, a sensor may be adapted to continuously monitor said assay while said incubator incubates said assay and said reader generates said test result. The sensor may be adapted to deactivate said incubator when said sensor detects an aberration on said assay. The sensor may be an optical detector. The optical detector may be adapted to detect a reflectance value. The assay may include at least one test zone and at least one control zone, and whereby said reflectance value is a comparison between a reflectance value at said test zone and a reflectance value at said control zone. Further, if the reader and/or incubator hood is opened during incubation or reading, a signal may generate a no-result response. Additionally, if said assay is removed before a test result is generated, a signal may generate a no-result response.

In some examples, the incubator may be deactivated when said sensor detects a reflectance value on said assay that is inconsistent with a predetermined theoretical reflectance value on said assay. For instance, a reflectance value on said assay that is inconsistent with said theoretical reflectance value may indicate an inadequate flow on said assay. Further, a reflectance value on said assay that is inconsistent with said theoretical reflectance value may indicate a prior analyte development on said assay. Similarly, a reflectance value on said assay that is inconsistent with said theoretical reflectance value may indicate a contaminated optical path.

In other examples, the sensor may be adapted to deactivate said reader when said sensor detects an aberration on said assay. The sensor may be an optical detector. The optical detector may be adapted to detect a reflectance value. The assay may include at least one test zone and at least one control zone, and whereby said reflectance value is a comparison between a reflectance value at said test zone and a reflectance value at said control zone. A no-result response may be generated when said sensor detects a reflectance value on said assay that is inconsistent with a predetermined theoretical reflectance value on said assay. A reflectance value on said assay that is inconsistent with said theoretical reflectance value may indicate an inadequate flow on said assay. Further, reflectance value on said assay that is inconsistent with said theoretical reflectance value may indicate a prior analyte development on said assay. Likewise, a reflectance value on said assay that is inconsistent with said theoretical reflectance value may indicate a contaminated optical path.

The sensor may be a decoding sensor. The decoding sensor may be chosen from a color sensor, a RFID reader, a barcode reader and a combination thereof. Typically, the sensor is triggered with an activation element chosen from a hood sensor, an incubator sensor, a trigger switch and a combination thereof.

The apparatus may include a housing that is adapted to substantially enclose said reader and said incubator. The housing may include insulation adapted to withstand deformation during said incubation. The housing may also include a cavity adapted to secure said assay and receive light from said reader. The cavity may include an optical aperture to receive light from said reader. The cavity may include an adjustable fastener adapted to position said cavity in an optical path with said reader. The cavity may include insulation adapted to withstand deformation during an incubation period. The assay may be a lateral, capillary-flow test strip. And thereby the housing may include a removable optical window adapted to block debris from said sensor. The removable optical window may include a handle. The removable optical window may be cleanable. Similarly, the removable optical window may be disposable. Additionally, the removable optical window may be slide-mounted. The housing may include an air opening. The air opening may include a cap.

In particular examples, the system may include a user interface. The user interface may include an integrated circuit board, for example to support a display board. The user interface may also be adapted to view flow development. Similarly, the user interface may be adapted to view the test result, including a no-result response. The user interface may also be adapted to view flow development after said reader has detected at least one flow development on said assay. By dynamically assessing development more often (about fifteen seconds or less) a positive result may be more quickly determined as a test result. For example, when the control line development reaches a predetermined value compared to the test line (such as a sustained difference in intensity) a positive result can be indicated. The control line will get darker as time passes and more flow (for example label) reaches the control line. A negative result can take longer to determine although the same theory applies. For example, in the extreme case of absolute zero contamination the negative test result can be determined more quickly than compared to a more borderline case.

In another embodiment, a lateral flow assay system to generate a test result from an assay includes an incubator that is adapted to incubate said assay and a reader that is adapted to read a diagnostic test on said assay. The assay may undergo a change when contacted with a sample to generate said test result.

In some examples, the system includes a removable assay module. The removable assay module may include an assay cavity adapted to align said assay with said reader. The assay may be a lateral flow test strip. Thereby, the assay cavity may be sized to receive said lateral flow test strip. The removable assay module may include a hood. The hood may enclose said assay in a closed testing position and expose said assay in an open access position.

Further, the removable assay module may include a bottom face adapted to align with at least one light aperture on said reader. The bottom face may include an adjustment fastener adapted to secure said assay cavity in an optical alignment with said reader. The bottom face may also include an engagement lip to position said bottom face with said reader. The removable assay module may include at least one optical window. The removable assay module may be adapted to be removed from said system and cleaned from debris.

In some examples, the incubator includes an insulated base. The incubator may be a temperature adjustable incubator. The temperature adjustable incubator may include at least one temperature control. Thereby, the temperature adjustable incubator may include localized temperature variations. For instance, the incubator may compensate for localized temperature variations. The incubator may compensate for localized temperature variations with an analog, proportional circuit. In other examples, the incubator may compensate for localized temperature variations with a digital control circuit, for instance by utilizing a PID algorithm or PID controller. Further, the temperature adjustable incubator may include an embedded temperature sensor. The temperature adjustable incubator may include a potentiometer. The incubator may include a heater. The heater may be chosen from a ceramic heater, a resister heater element and the like. Similarly, the incubator may include a cooling system. In yet other examples, the incubator incubates said assay in a means for creating an incubation environment.

The reader may perform continuous image detection of said assay to generate said test result. The continuous image detection may include monitoring a pre-flow development along said assay, including monitoring for excessive flow and inadequate flow along said assay. The reader may include a light source oriented in a predetermined pattern with respect to said assay. The light source may include a first mirror below said light source. The light source may include a focusing lens adapted to receive light from said first mirror. Further, the light source may include a second mirror positioned to direct light from the focusing lens to said reader.

In particular examples, the reader may include a sensor. The sensor may be an optical detector that is aligned with a light source for detecting transmission of light through said assay. For instance, transmission embodiments herein may include analysis of refracted light from the assay. The sensor may be a decoding sensor. The decoding sensor may be adapted to decode at least one reference code having a corresponding testing sequence on said assay. Further, the reader may include multiple channels. Each of said channels may include an associated feature chosen from a standard curve, a does-response curve, a positive cutoff value, a negative cutoff value and the like.

In yet further embodiments, a method of generating a test result from an assay includes incubating said assay in an incubation environment and reading a diagnostic test on said assay concurrently as said incubator incubates said assay. The method may include sensing said assay continuously while said incubator is incubating said assay. The method may include deactivating said incubator when sensing an aberration on said assay. The method may include removing a removable assay module, for example for cleaning debris, or the like, from said assay module. The method may include adding a test sample to a test medium to create said assay. The method may also include enclosing said test medium within said reader. The method may include positioning a sensor relative to said test medium so that a change on said test medium is detectable by said sensor. The method may include decoding a reference coding on said assay. Thereby, the method may include selecting a channel in said reader corresponding to said reference coding on said assay. Further, the method may include incubating said assay within the incubator according to said reference coding on said assay.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
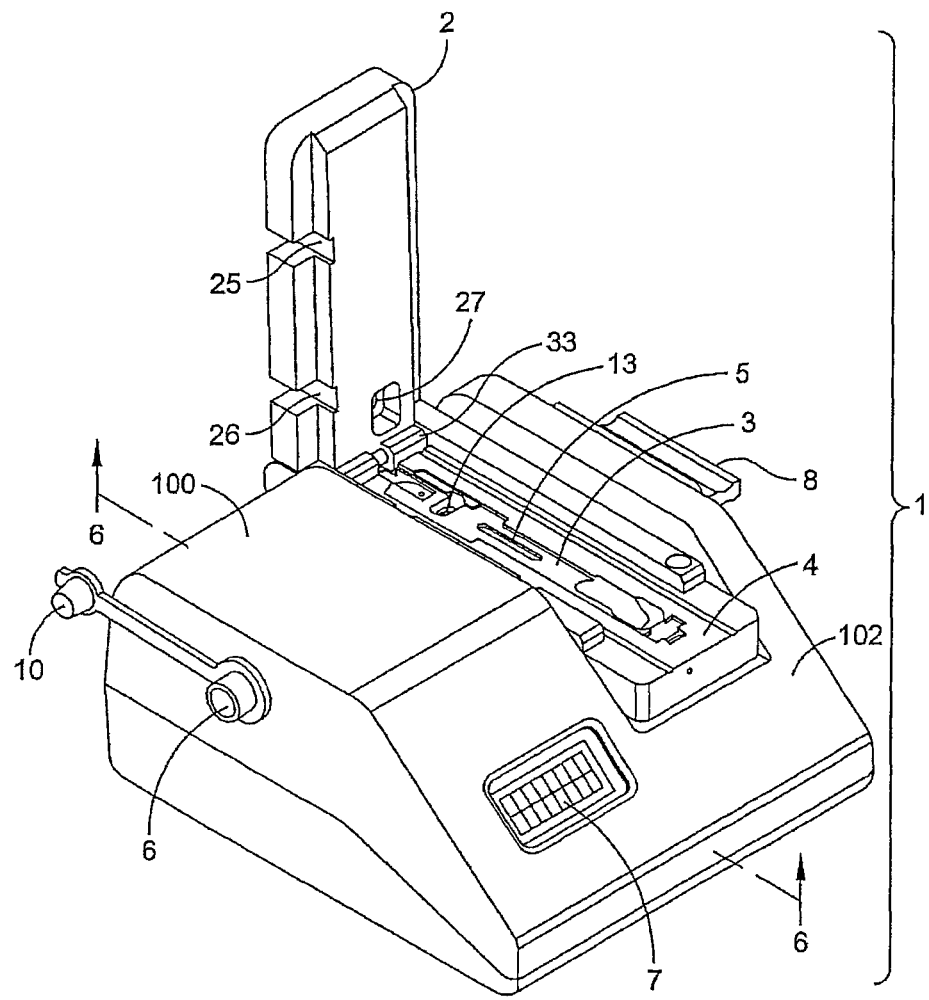
FIG. 1 is a front perspective view of one embodiment of a lateral flow assay system, with an open hood illustrating cavity and base components.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms. It will be understood that the illustrations are for the purpose of describing embodiments of the disclosure and are not intended to limit the disclosure or any invention thereto.

As introduced in FIG. 1, a lateral flow assay system 1 is shown embodied according to the present disclosure. Lateral flow assay system 1 includes a combined reader 100 and incubator 102. Reader 100 typically includes an imaging detector, such as a sensor, while incubator 102 typically includes an insulated base 4. In some embodiments, the insulated base is a removable assay module 104. Typically, reader 100 first monitors an assay for one, or more, monitoring values, including flow rate, prior analyte development and debris. In various examples, if a proper monitoring value is detected by system 1, incubator 102 incubates the assay and reader 100 generates a test result. However, if an inconsistent monitoring value is detected, system 1 may generate a no-result response.

As shown in FIG. 1, lateral flow assay system 1 is configured to receive an assay and analyze the assay to generate a diagnostic test result. Typically, the assay is a capillary-flow test strip. However, it is within the sprit of this disclosure for any of the assays herein to be other lateral flow assays.

FIG. 1 shows a housing enclosing the reader 100 and incubator 102 as an integral diagnostic unit. Other embodiments include a housing that partially encloses components of lateral flow assay system 1. Typically, the reader includes cavity 3 to receive the assay, and a hood 2 to enclose the assay. The housing may have an exterior and interior, and may be opened, for instance hood 2, to receive an assay into cavity 3. As illustrated in FIG. 1, hood 2 may be lifted and the assay inserted into a heating cavity such as a metallic, for example aluminum, cavity within incubator 102. Typically, cavity 3 is surrounded by insulating material, such as a plastic material, for example a thermoplastic such as polyoxymethylene, known as Delrin (DELRIN is a registered trademark of DuPont) to insulate cavity 3, and does not deform when heated to the temperatures required for generating a test result.

As shown in FIG. 1, hood 2 may be opened into an access position to receive and/or remove an assay within cavity 3 of insulated base 4. Hood 2 may also be configured to substantially seal cavity 3 to enclose the assay in a closed testing position. Openings 25, 26 and 27, in hood 2 allow access to adjustment fasteners 11, 12 and 13 (see FIG. 8), including screws and the like, when hood 2 is in a closed position. In other examples, adjustment fasteners may also be accessed when hood 2 is positioned in an open access position. Typically, adjustment fasteners align cavity 3 in relation to optics, for instance an imaging detector described hereinafter, so that changes on the assay may be detected. For example, test strips may have multiple line developments in various areas on the test strip, as described hereinafter and introduced in FIG. 7. By allowing fine cavity adjustment with the adjustment fasteners through openings 25, 26 and 27, costly and cumbersome system recalibration may be minimized, or avoided. For instance, depending on a particular assay, flow, test and control lines may be in a variety of different position along the assay, as explained below, which may trigger an unexpected reflection, or transmission, value if cavity 3 is not properly adjusted.

As introduced above, cavity 3 may be configured to receive the assay, such as a lateral flow test strip, to position and maintain the assay in an optical alignment with reader 100. In some examples, cavity 3 is shaped with an elongated channel, for instance to receive a lateral, capillary-flow test strip.

Some embodiments of reader 100 are optical analysis readers, which often include a light source and an imaging detector, for example a sensor, that is aligned such that the light from the light source shines onto the assay and is then reflected onto the imaging sensor. An example of optical reader components useful in embodiments herein is described in U.S. Pat. No. 6,124,585 (Apparatus for measuring the reflectance of strips having non-uniform color), issued Sep. 26, 2000 and in PCT/US 11,49170 (Lateral Flow Assay Analysis), filed Aug. 25, 2011, both of which are incorporated herein by reference. Typically, the presence and, in some cases, the concentration, of an analyte on an assay may be determined by measuring, for instance, the optical reflectance from an area of development on the assay. In some examples, percent reflectance may be used to determine the result. In other examples, transmission may be used to detect the result. For instance, the assay may be transparent and include a surface having a transmission profile, similar to the reflectance profile discussed below. This structure and function described in that patent may be adapted by those of ordinary skill in the art in accordance with the disclosure herein to obtain a functioning unit.

Reader 100 may comprise a variety of light sources, including an incandescent bulb, a fluorescent tube, a light emitting diode or the like. In some examples, the light source may be an array of discrete light sources, for instance colored light emitting diodes chosen from red, green, blue and a combination thereof. In yet other examples, the light source may be an individual light source, for instance a singular diode. Typically, the light source is configured and current driven to emit an illumination pattern suitable for reflecting onto the assay, for instance along an elongated test strip. As shown in FIG. 1, light can be directed to the assay, for example through aperture 5 in cavity 3, and then reflected off the assay, back through the cavity aperture 5 and directed to an optical detector.

In one example, an optics circuit board 31 (see FIG. 6) may have a plurality of light emitting diodes (LEDs) mounted thereon, for instance in a predetermined pattern around light-emitting aperture 5. The LEDs may be mounted on one side of optics circuit board 31. An optical detector array may be mounted to the reverse side of the same optics circuit board 31. Further, a first mirror may be positioned below the light-emitting aperture at a pre-determined angle, for instance about three hundred and fifteen degrees, to circuit board 31. A second mirror may be positioned beneath the optical detector, for instance at an angle of about two-hundred and twenty degrees to circuit board 31, such that a substantially 90-degree angle exists between first and second mirrors. A focusing lens may be positioned between the first and second mirrors. Thereby, the light emitted from the LED array may illuminate an assay and then light is reflected therefrom through light-emitting aperture 5, for instance to the first mirror, from the first mirror through the focusing lens to the second mirror, and from the second mirror onto the optical detector. In that respect, the light striking the optical detector may cause the optical detector to generate a measurable voltage. In some examples, the optical detector can output a data stream that can be converted, for example by an on onboard central processing unit, into a series of 128 distinct one-dimensional numeric readings. The 128 readings can be taken multiple separate times and averaged.

In additional examples, a light processor may be coupled to the light source to actuate the light source and provide each light with the appropriate current to generate the desired emission pattern. The light processor may be used to read and store data from the optical detector. The light processor may also be used to adjust the output of an array of discrete light sources such that the emission pattern striking the light detector array has a uniform intensity. The lighting processor may include data storage for said desired light-emission pattern.

Further, the light source may be an LED light source, including a red, green, blue LED device in a single package. For instance, the LED light source for the color sensor can also be three discrete LEDs. Similarly, a single white LED and three discrete photodiodes, with narrow bandwidth responses at the red, green and blue wavelengths, can be used as a detector front-end.

In yet other examples, one LED is used with an optional feedback loop. The feedback loop can use a photodiode to sense light output variation from the single LED. If light output changes, a signal is sent so that an appropriate adjustment can be made, for example, an increase or decrease in current to the LED. Reflectance changes can be the result of the binding of a label, including color particles such as gold beads. Reflectance changes may also be a result of contaminants and interferences in the optical path.

Figure 2:
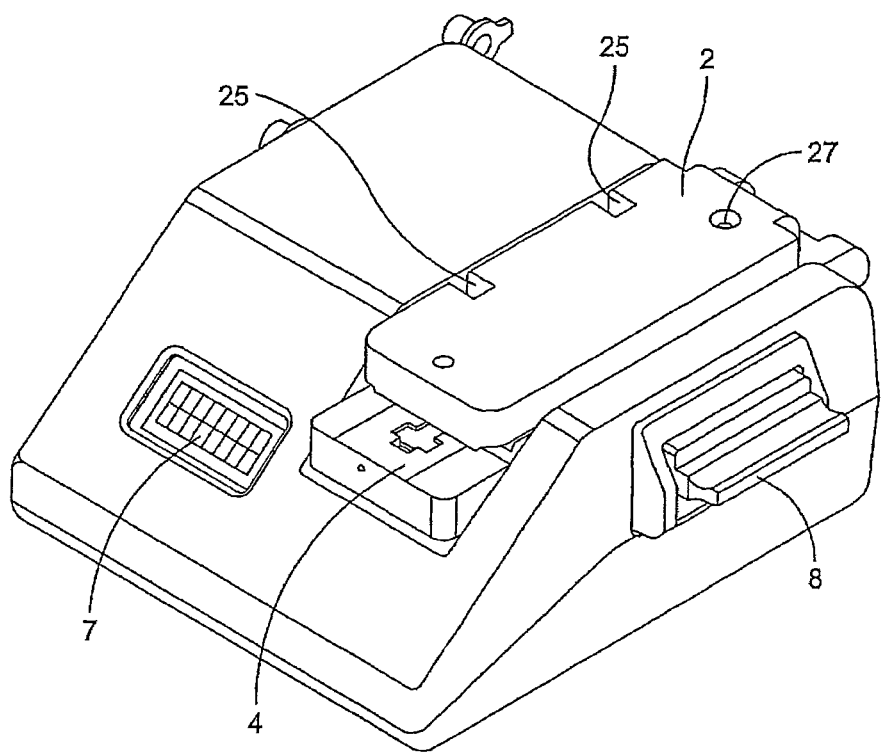
FIG. 2 is a front perspective view of the lateral flow assay system embodiment of FIG. 1, with the hood in a substantially closed position.

As seen in FIG. 2, optical window 8 may be positioned between the assay and reader 100, for instance between a test strip and a sensor. Typically, optical window 8 blocks debris from the assay from contaminating the imaging detector itself, or other system parts used with the sensor, such as lenses and mirrors. In some examples, optical window 8 is clear and includes a handle so that optical window 8 is removable from reader 100 for cleaning. In other examples, the removable optical window may be disposable. In one example, the window material includes clear polyvinyl chloride (PVC) plastic. Window 8 may be mounted on a slide and inserted into reader 100 between cavity 3 and the sensor. The figures show only one removable and cleanable window to block debris, however, other embodiments include additional optical windows covering to protect portions of the optics and/or incubator 102 components.

Regardless of the presence of an optical window, it is possible that dust and debris will infiltrate into reader 100, for example the optical sensor mechanism. To provide an additional cleaning option, air inlet 6 can be provided for compressed air. Air inlet 6 may be covered with a tethered cap 10. In use, clear, optical window 8 is removed, and tethered cap 10 is detached. Compressed air is then blown through reader 100, so that debris collected on, or near, the reader sensor is blown out through the opening previously occupied by window 8.

Some embodiments of reader 100 are programmed with multiple channels, each of which may have separate parameters associated with a related diagnostic test. Each channel selection parameter may include a standard curve, a doses-response curve and the like.

Figure 3:
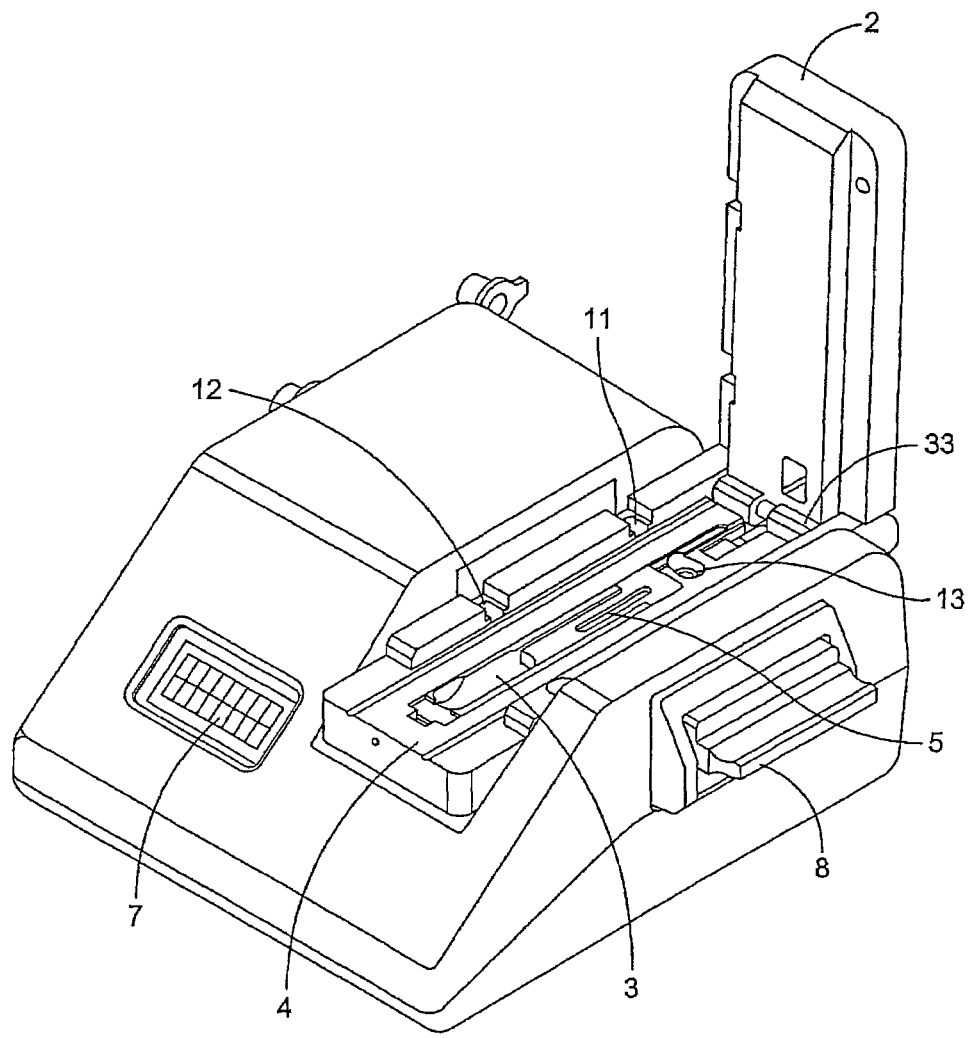
FIG. 3 is a front perspective view of the embodiment of FIG. 1, illustrating examples of cavity and adjustment components.

FIG. 3 shows cavity adjustment fastener 13 in cavity 3, and base adjustment fasteners 11 and 12 in insulated base 4. Openings 25, 26 and 27, in hood 2 allow access to adjustment fasteners 11, 12 and 13, including screws and the like, when hood 2 is in a closed position. In other examples, adjustment fasteners may also be accessed when hood 2 is positioned in an open access position. Typically, cavity adjustment fastener 13 aligns cavity 3 in relation to optics, for instance an imaging detector described hereinafter, so that changes on the assay may be detected.

Figure 4:
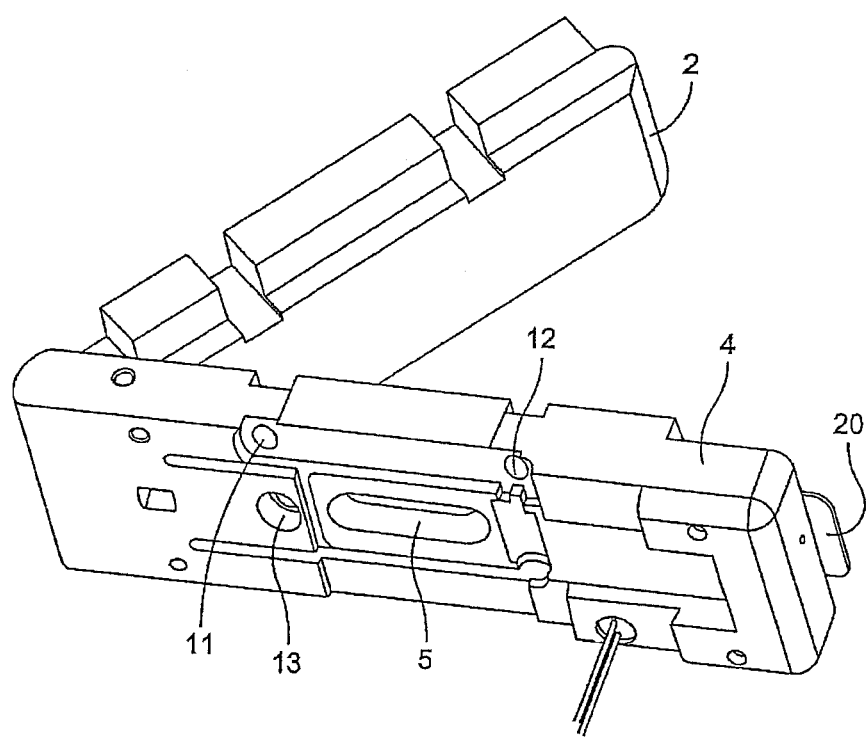
FIG. 4 is an isolated side perspective view of assay base module elements.

FIG. 4 shows one example of insulated base 4 and hood 2 in an opened access position. As shown, the bottom face of base 4 includes openings for cavity adjustment fastener 13, openings for base adjustment fasteners 11 and 12 and light-emitting aperture 5.

Figure 5:
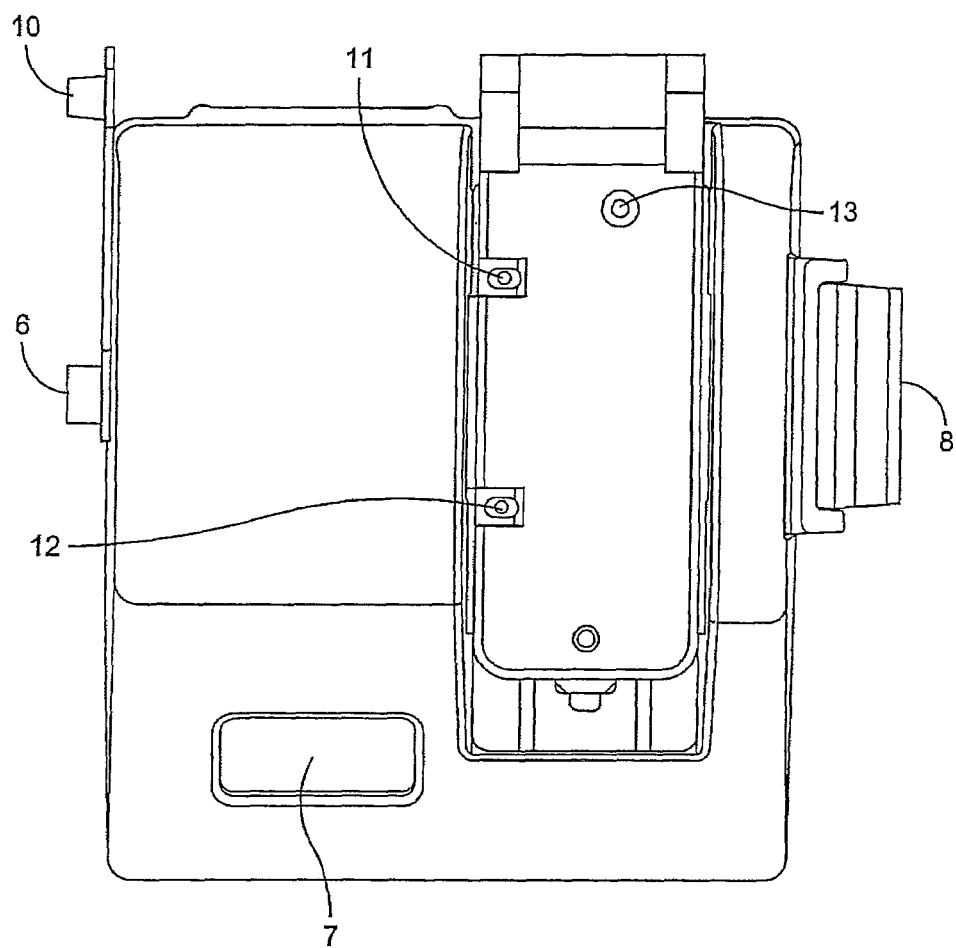
FIG. 5 is a top view of the lateral flow assay system embodiment of FIG. 1 in a closed position.

FIG. 5 shows a top view of lateral flow assay 1 with hood 2 in closed testing position. Window 8 is positioned on the side of the housing to allow the user to remove window 8 for cleaning. As introduced above, air may be inserted through air inlet 6 to further clean debris from optic components.

Figure 6:
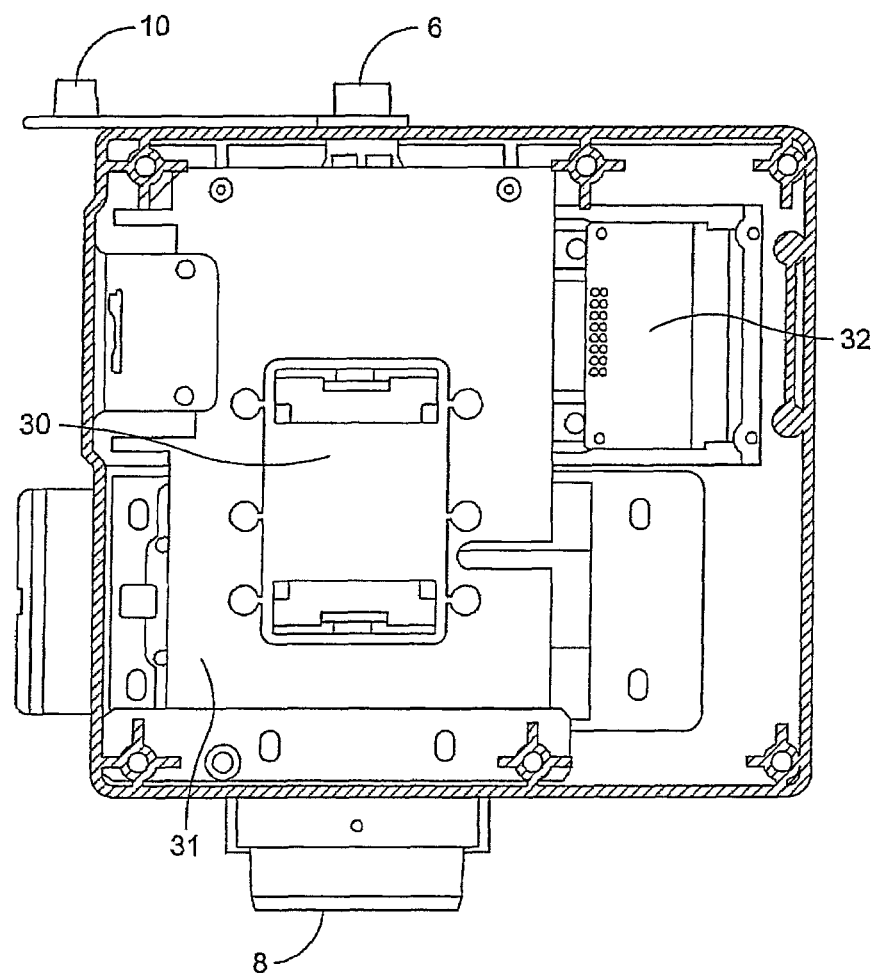
FIG. 6 is a sectional view of the lateral flow assay system embodiment of FIG. 1 taken along lines 6-6, showing circuit board components.

FIG. 6 is a bottom schematic view showing optics board 30, circuit board 31 and display board 32. As shown, LEDs may be mounted on one side of optics circuit board 31. Further, as shown throughout the various figures, lateral flow assay system 1 may include user interface 7. User interface 7 includes an integrated circuit board 31 supporting a display board 32. In one example, user interface 7 allows a user to view flow development. Further, user interface 7 may allow a user to monitor a subsequent flow development after reader 100 has already detected at least one flow development on the assay. Similarly, user interface 7 may display a final test result, including a no-result response.

In some embodiments, user interface 7 may graphically assess and illustrate the assay development results, including for example test results at control lines and test lines for one, or multiple, analytes. In such embodiments, the system detects the assay's diagnostic test development about every fifteen seconds; however other embodiments include detecting the assay development more often than every fifteen seconds, including about ten seconds and less than about five seconds. As illustrated later in FIGS. 15-18, the graphical display of the assay development includes at least one valley for a test line 40 and at least one valley for a control line 42. Typically, the valleys indicate that line development is a reduction in reflectance from the assay, for instance against a lateral flow test strip. Further, in some examples, reader 100 additionally determines a low point in the valley (as later illustrated in FIGS. 15-19) by determining a lowest reflectance point with respect to a reflectance background base. Generally, by dynamically assessing diagnostic development at intervals of about fifteen seconds, a positive result may be more quickly assessed than compared to traditional methods. For instance, as development along control line 42 reaches a certain value compared to development along test line 40, i.e. a sustained difference in intensity, a positive result may be established because more flow (including label) may reach control line 42.

Figure 7:
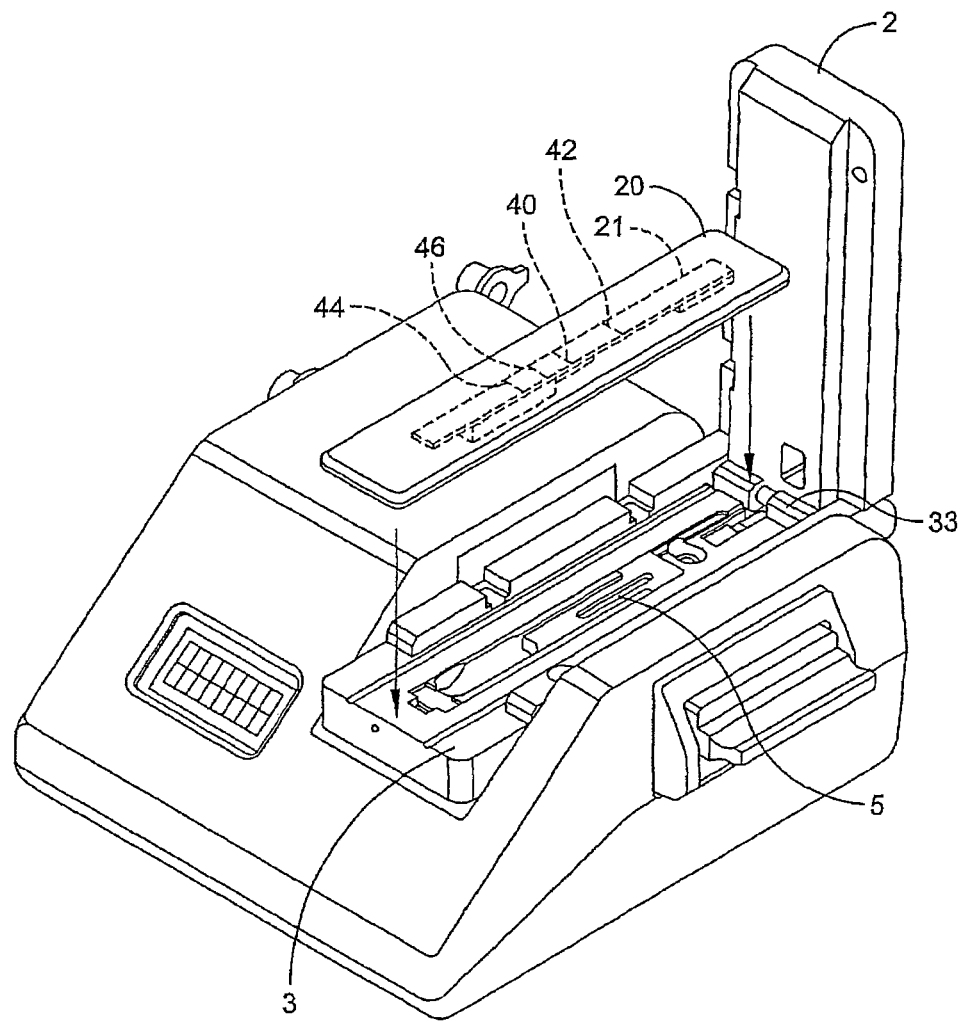
FIG. 7 is a front perspective view of one embodiment of a lateral flow assay system and assay components.

FIG. 7 illustrates one embodiment of hood 2 in open access position with assay 21 secured within test strip enclosure 20, which is adapted to be received by cavity 3. Examples of assay elements for particular diagnostic tests having components useful for embodiments herein include those described in U.S. Pat. No. 7,410,808, issued Aug. 12, 2008; U.S. Pat. No. 7,097,983, issued Aug. 29, 2006; U.S. Pat. No. 6,475,805, issued Nov. 5, 2002; U.S. Pat. No. 6,319,466, issued Nov. 20, 2001; U.S. Pat. No. 5,985,675, issued Nov. 16, 1999 and U.S. patent application Ser. No.

11/883,784, filed Aug. 6, 2007, all of which are hereby incorporated herein by this reference.

Generally, lateral flow assay 21 is membrane-based test device, in which a sample that is suspected of containing the analyte of interest is placed at or near one end of the membrane strip. The sample is carried to the opposite end of the membrane strip by a mobile phase that traverses the membrane strip, for example by capillary action. While traversing the membrane strip, the analyte in the test sample, if any, encounters one or more reagents. The reagents can include binders for the analyte. Binders can be mobile and, therefore, flow with the sample or be immobilized on the test strip as a capture agent. Depending on the test configuration, either the analyte binder, the analyte itself, or some other reagent in the test system, will be captured by the immobilized capture agent and, thereby, produce a detectable signal. The signal can be generated by a label provided within the assay. The detectable signal can be measured, such as by optical reader 100.

Assay 21 may include at least one test line 40 in a test zone and at least one control line 42 in a control zone. A theoretical reflectance value may be a comparison between a reflectance value at test line 40 and a reflectance value at control line 42. A pre-set difference between a theoretical reflectance value at test line 40 and a theoretical reflectance value at control line 42 may activate lateral flow assay system 1, including reader 100, to generate a test result. Further, a separate pre-set difference between a theoretical reflectance value at test line 40 and a theoretical reflectance value at control line 42 may trigger an error. Triggering of the error may cause the microprocessor to withhold a test result, including generating a no-result response, or deactivating reader 100 and/or incubator 102. Other embodiments include a comparison between a transmission value at test line 40 and a reflectance value at control line 42.

A reflectance value on the assay that is inconsistent with the theoretical reflectance value may indicate an inadequate flow in the mobile phase on the assay. For instance, assay 21 may have a flow line 44 with a corresponding theoretical light reflectance measurement. A no-flow development value may be a reflectance value of about 85 on a reflectance scale. Such an inadequate flow may trigger a detectable signal to generate a no-result response. Additional examples include deactivating the lateral flow assay system 1, including deactivating reader 100 and/or incubator 102. In other examples, the flow reference area may include both an intermediate flow reference line 46 with a corresponding theoretical reflectance value and a flow reference line 44.

Similarly, a reflectance value on the assay that is inconsistent with the theoretical reflectance value may also indicate a prior analyte development on the assay. Such a prior analyte development may trigger a detectable signal to generate a no-result response. Further, if the assay is removed prior generating a test result, system 1 may generate a no-response result.

In some embodiments, assays 21 also include a coding reference component with a corresponding testing sequence for lateral flow assay system 1. The coding may be, for example, a color coding, a bar code, an RFID tag or the like, and may be positioned anywhere along the assay so that decoder sensor can decode the reference code, for example on the assay's surface. For instance, in some examples, the coding reference is positioned along the distal end of assay 21. Depending on the type of coding on the test strip, reader 100 may require an integrated decoding sensor for example, a bar code reader, an RFID decoder or a color sensor.

Typically, the testing sequence is at least one temperature adjustment parameter within incubator 102 and/or a channel selection of reader 100. Further, the reader test parameter may include an associated feature chosen from a standard curve, a does-response curve and the like. Other embodiments include a variety of testing sequence parameters for the associated diagnostic test being run on the assay.

In some examples, a color matrix, or matrices, reference coding, including a color chosen from red, blue, green and combination thereof, may be associated with a corresponding diagnostic test parameter. When a color coding is used on assay 21, the color can be read by the reader either by a separate optical reading system or the same system that reads the test result. That is, the assay can include a color portion that, after enclosure within the system and test initiation, will be read by the color sensor to determine the reader channel and/or the appropriate incubator temperature. For example, a photodiode with a wide dynamic range of sensitivity to red, green and blue wavelengths can be used as the detector. Red, green and blue LEDs can be used as the light source. Each LED can be turned on sequentially and the detector used to determine the reflectance of each of the colors. A black surface (totally absorbent as containing no color) will produce no reflectance of the given LEDs wavelength and, therefore, the detector will produce low output readings. A white surface will produce maximum reflectance of all three LEDs. Various colors (depending on its content in the surface measured) will produce output from the detector at varying levels.

Such color sensor component may be configured as a separate sensing component within reader 1, or depending on the sensor used to read the test strip result, a singular component that detects both development on the test strip and color coding. In various examples, assays may be coded with a color that defines the test being run. For example, a red color can indicate a test strip to be used to detect beta-lactam antibiotics. Various matrices can also be delineated by the color system. In the red example, after system 1 detects the red color on the test strip, reader 100 and/or incubator 102 may be automatically configured for that specific assay 21, for example by temperature adjustment of incubator 100 and selection of appropriate reflectance test parameters within reader 102. Therefore, in some embodiments, system 1 may an integral diagnostic test unit that is triggered by specific reference codings on the assay.

In other examples, the coding reference may comprise a radio frequency identification (RFID) tag. Such radio frequency signal transmits a signal from the tag to a decoding RFID sensor module. This signal can be used to start the analytic testing sequence, event, channel, temperature or the like in the reader and/or incubator. Similarly, the reference coding may be a bar code, wherein the bar code is placed on the assay and a bar code reader decodes the reference coding and associated testing sequence information.

Figure 8:
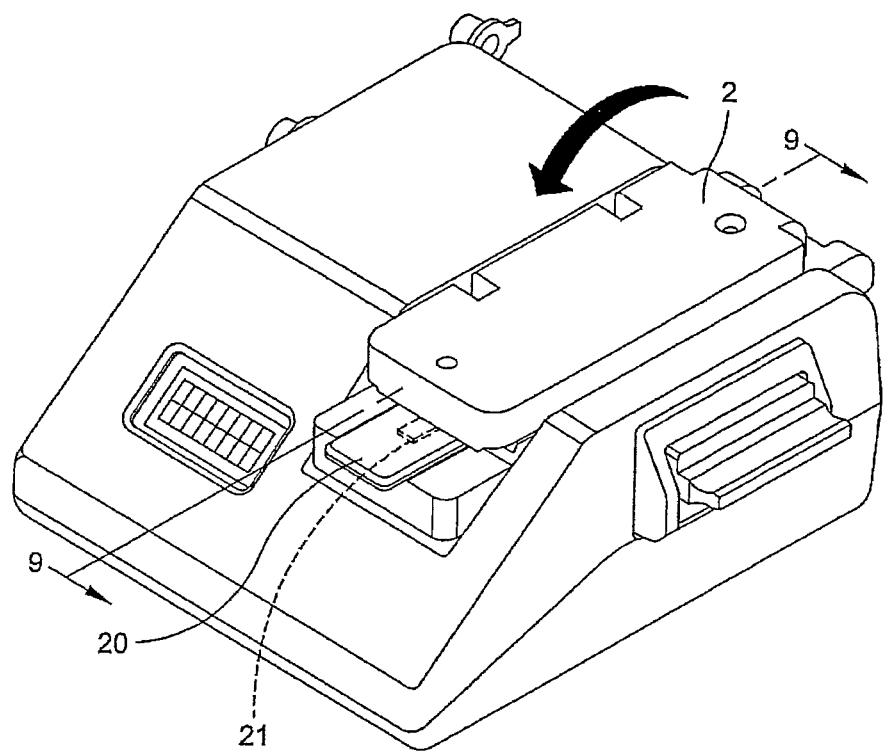
FIG. 8 is a front perspective view of the embodiment of FIG. 7 in a closed position.

FIG. 8 shows assay 21 and assay enclosure 20 positioned within the reader, with hood 2 in a closed position. As shown, hood 2 is pivoted down in a closed testing position, wherein a sensor in the reader is in an optical alignment with assay 21 to generate a test result or a no-result response.

In the closed testing position, incubator 102 may incubate assay 21 in an incubation environment. For instance, incubator 102 may heat and/or cool assay 21 to provide the proper incubation environment for a corresponding assay and diagnostic test. Typically, incubator 102 is in communication to the cavity 3 and is capable of maintaining a consistent temperature within cavity 3 either by heating or cooling at a pre-defined rate. In some examples, incubator 102 includes insulated base 4. In other examples, incubator 102 incubates removable assay module 104, as described hereinafter. The incubator may be a temperature adjustable incubator. In these examples, the temperature adjustable incubator may include a temperature control. In additional embodiments, the temperature adjustable incubator may allow for localized temperature changes.

Incubator 102 may include a heater. The heater may be a ceramic heater, a resister heater element and the like. Typically, cavity 3 is designed to be small so that the heater need only draw minimum current. In that way, heating only essential areas and providing insulation around those areas minimizes power requirements. Use of various heating algorithms can be useful. For example, a proportional integrated derivative (PID) can be used. In other examples, incubator 102 may compensate for localized temperature variations from the selected target temperature, for instance a target temperature according a corresponding testing sequence. Incubator 102 may also compensate for localized temperature variations with an analog, proportional control circuit. In other examples, incubator 102 may also compensate for localized temperature variations with a digital control circuit, for instance by utilizing a PID algorithm or a PID controller. Further, those of ordinary skill would recognize that PI, PD, P or I controllers, and/or algorithms, do not preclude any of the inventions herein. For instance, temperature adjustable incubator may include a digitally controlled potentiometer to allow the microprocessor selection of temperature. In other examples, algorithms are particularly useful when test results are affected by small temperature variations. Embodiments include incubator control systems that eliminate the need for manual adjustment by use of embedded, digital temperature sensors and digital potentiometer that provides both accurate temperature reporting and a mechanism by which a micro-controller can adjust a stand-alone, analog, incubator control circuit.

In additional embodiments, cooling might be advantageous to reduce the incubation environment temperature, for example to stabilize the environment of a test medium and/or sample prior to incubation.

Figure 9:
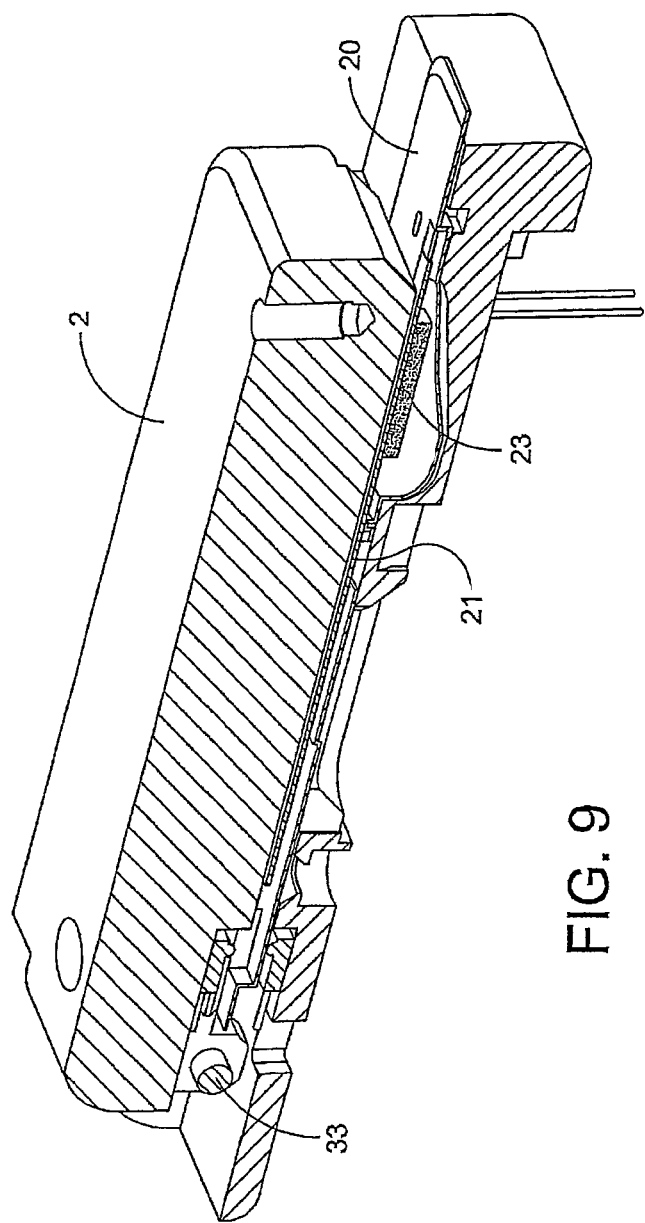
FIG. 9 is a partial cross-section of one example of the embodiment introduced in FIG. 7 taken along 9-9.
Figure 10:
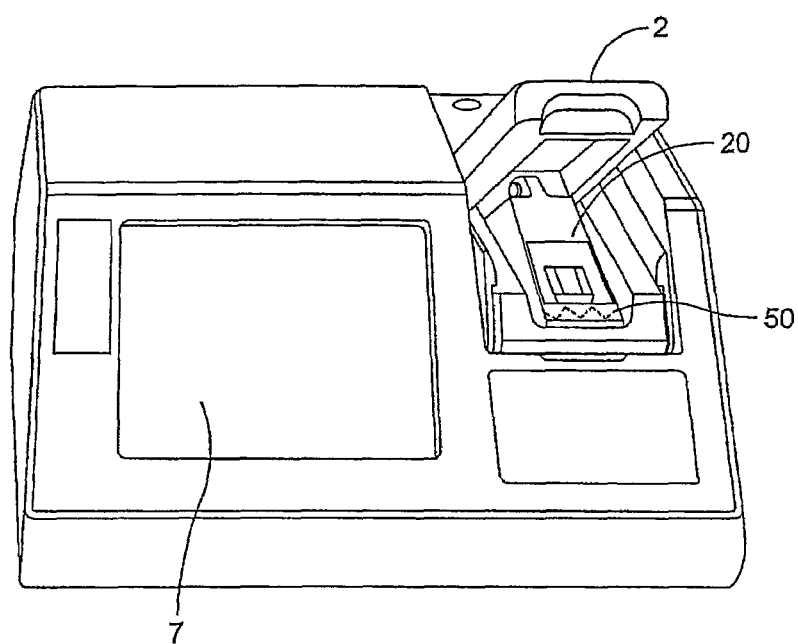
FIG. 10 is a front perspective view of one embodiment of a lateral flow assay system and assay components.
Figure 11:
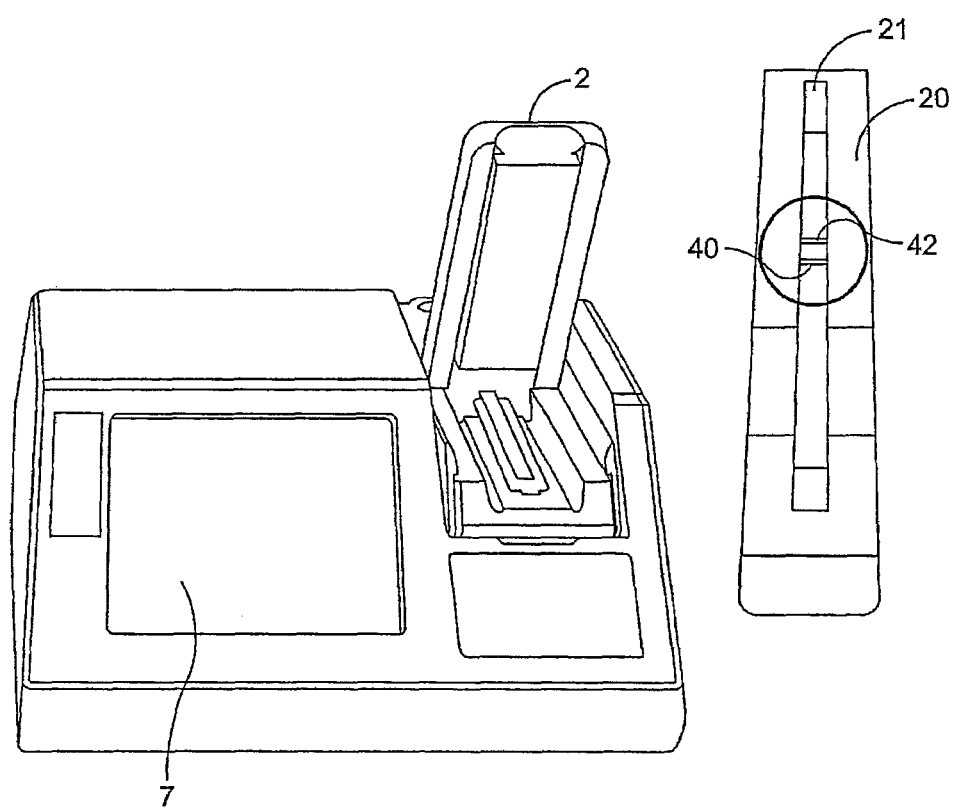
FIG. 11 is a front perspective view of one embodiment of a lateral flow assay system and assay components.

As shown in FIG. 9, test strip 21 may include a first end having a sample absorbing material 23. Further, as introduced in FIG. 10, test strip 21 may have a peel strip 50 to introduce sample onto sample absorbing material 23. Peel strip 50 may include a peel tab at one end of peel strip 50 to facilitate movement of said peel strip 50. Sample absorbing material 50 may be sized and configured to receive about 0.1 to about 1.0 mL of a fluid. Further, sample absorbing material 50 may be composed a dry cellulosic material. Other embodiments include other materials of sample absorbing material 50.

Figure 14:
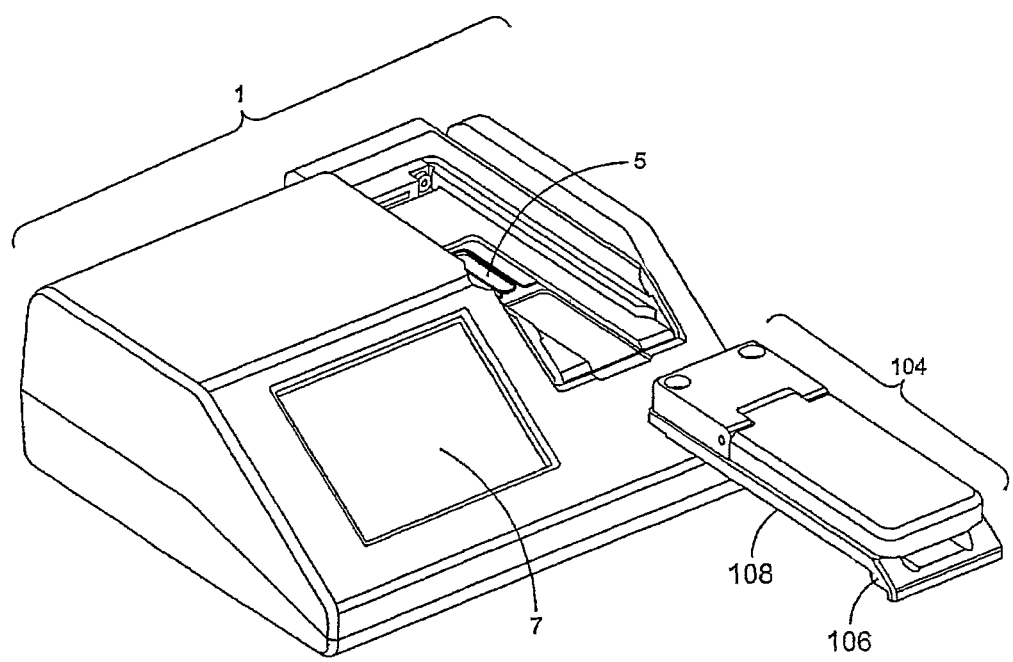
FIG. 14 is a front perspective view of one embodiment of a lateral flow assay system having a removable assay module.

Typically, assay 21 also includes an opposed second end having a reactor detector material. Assay 21 may support a releasing area having a mobile phase receptor for the at least one analyte. Further, assay 21 may be sized and adapted to be enclosed within test strip cavity 3. Similarly, assay 21 is typically sized and adapted to be enclosed, for example enclosed tightly, within an assay cavity 3 of a removable incubation module 104, as seen in FIG. 14. Typically, assay 21 is adapted for selecting the detection of a diagnostic test group chosen from an antibiotic analyte, toxic analyte, analyte class, a combination thereof and the like.

Reader 100 may include a sensor to monitor a test progress, for example on a lateral flow assay, and/or determine a test result from the lateral flow assay. The sensor is positioned relative to assay 21, so that a change on assay 21 can be detected by the sensor. Typically, the sensor is activated when the lateral flow assay is both positioned within cavity 3 and exposed to the consistent temperature within cavity 3 from incubator 102. For example, the sensor can be activated by closing hood 2 that encloses cavity 3. The sensor may include an optical detector and a microprocessor. Typically, the optical detector is aligned in an optical path with the assay and is adapted to acquire an image detection on the assay and is performing a continuous image detection acquisition of the assay.

The sensor may be a single photodiode, multiple photodiodes, a linear photodiode array, a charged couple device, a complementary metal oxide semiconductor and a combination thereof. Therefore, at the same time as incubation and flow, or before, or after incubation and flow is complete, the optical sensors can monitor the assay and compare optical readings, such as reflectance and/or transmission readings, to determine various aspects including sample flow, interference with the optical path such as by debris in the optical path, line development and test result. When the assay and line development falls within preset parameters, the test can continue to completion and provide a final result. Checking of the assay by the optical sensor prior to test completion can provide the user with additional confidence that the test was processed properly.

Typically, the output may be a voltage, current or a digital output proportional to light intensity as determined by signal conditioning circuitry. Some examples of reader 100 include the TSL12T and TSL13T sensors available from TAOS (Texas Advanced Optolectronic Solutions). The TSL12T and TSL13T sensors are cost-optimized, highly integrated light-to-voltage optical sensors, each combining a photodiode and a transimpedance amplifier (feedback resistor=80 MΩ and 20 MΩ respectively) on a single monolithic integrated circuit. The photodiode active area is 0.5 mm×0.5 mm and the sensors respond to light in the range of 320 nm to 1050 nm. Output voltage is linear with light intensity (irradiance) incident on the sensor over a wide dynamic range.

In some examples, the microprocessor may be in communication with the optical detector, and in particular with the sensor. In other examples, the optical detector outputs to other logic means. Further, the microprocessor may be adapted to signal the optical detector to perform continuous image detection of said assay to generate said diagnostic test result. The microprocessor may include, or have associated, memory to store information corresponding to an imaging parameter. The memory may include instructions for monitoring a pre-test analysis on the assay and for generating a diagnostic test result on the assay.

In some embodiments having assays with coding references, as discussed herein, the optical detector may have a decoding ability to decode a reference code on the assay. Thereby, the decoding sensor may thereby active a corresponding diagnostic test in reader 100. For instance, the decoding sensor may activate a corresponding channel in a multichannel reader 100 and/or activate a corresponding incubation temperature profile within incubator 102.

The decoding sensor may be a color sensor. For example, the color sensor may be a photodiode with sensitivity to wavelengths chosen from red, blue, green and a combination thereof. In such an example, a color reading an arrangement of photodiodes, each with a specific color filter, is used as the decoding sensor and a white LED (which provides a wide spectrum of light through the 3 bandwidths (Red, Green and Blue)) is used as the light source. When the LED is turned on, the output from each of the photodiodes is obtained to determine the reflectance of that specific color. The decoding sensor may also be an RFID reader or a bar code reader.

Although reference is often made herein to optical reflectance, and optical reflectance readers, a variety of readers may be usefully employed including, for example, transmittance reader, fluorometers, luminometers, bar code readers, radiation detectors (such as scintillation counters), UV detectors, infrared detectors, electrochemical detectors or optical readers, such as spectrophotometers, charged coupled device (CCD) or complimentary metal oxide semiconductor (CMOS) can be used as an image sensor. An optical reflectance reader can be programmed to analyze the test strip through two-dimensional readings, rather than through the one dimensional, 1×128, readings. For example, a 5×128 or 512×492 matrix of "pixels." Such a 2-dimensional reading widens the reflectance capture area to capture reflectance directly from the sides of the test strip.

In other examples, a transmittance reader, such as an ultraviolet Visible Near-Infra red (UV-Vis-NIR) spectroscopy may provide a characterization of the absorption, transmission, and/or reflectivity of the assay. For instance, such an analytical technique may measure the amount of light absorbed on the assay at a given wavelength. Those of ordinary skill in the art would appreciate that a molecule, or part of a molecule, can be excited by absorption. Typically, organic chromophores which absorb strongly in the UV or visible portions of the spectrum nearly always involve multiple bonds, such as C=C, C=O or C=N. This molecular excitation energy may be dissipated as heat, for instance kinetic energy, by the collision of the excited molecule with another molecule, e.g., a solvent molecule, as the molecule returns to the ground state. In other embodiments, the excitation energy may be dissipated by the emission of light via fluorescence. Regardless of the process, an excited molecule may possess any one of a set of discrete amounts of energy, for instance as described by the laws of quantum mechanics. In examples herein, the major energy levels may be determined primarily by the possible spatial distributions of the electrons, and to a lesser extent by vibrational energy levels, which arise from the various modes of vibration of the molecule.

Therefore, in particular examples herein, absorbance measurements may be determined by the concentration of a solute on the assay. For instance, the progress of such a chemical reaction may be followed using a spectrophotometer in reader 100 to measure the concentration of either a reactant or a product over time. In other examples, a transmission spectroscopy may be used for solid, liquid, and gas sampling. Typically, light is passed through the assay and compared to light that has not. The resulting spectrum may depends on the pathlength or sample thickness, the absorption coefficient of the sample, the reflectivity of the sample, the angle of incidence, the polarization of the incident radiation, and, for particulate matter, on particle size and orientation.

Figure 12:
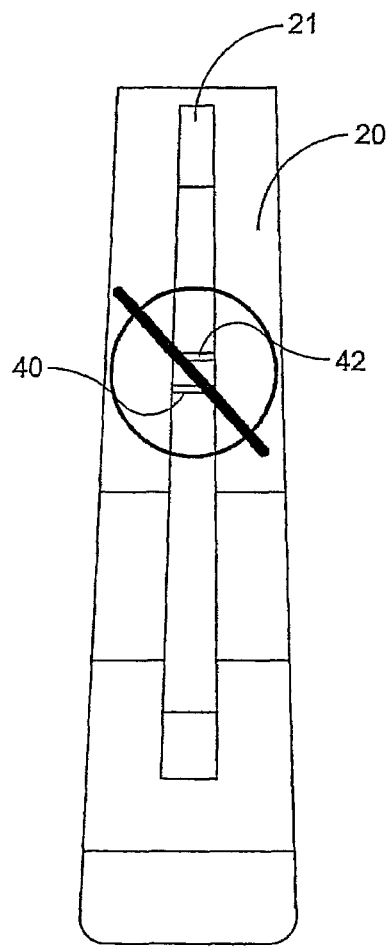
FIG. 12 is an isolated view of the assay illustrated in FIG. 11, showing one example of a prior analyte development before testing triggering an error.

In some embodiments, the sensor monitors assay 21 for prior analyte development before generating a test result. As shown in FIG. 12, prior analyte development on test line 40 and control line 42 indicates an error. For instance, assay 21 may have a theoretical reflectance value that is a comparison between a reflectance value at test line 40 and a reflectance value at control line 42. A reflectance value on assay 21 that is inconsistent with the theoretical reflectance value may indicate a prior analyte development on assay 21, including a pre-run assay, contaminated assay or the like. The prior analyte development may trigger a detectable signal to generate a no-result, for instance a no-run, response and/or deactivate assay system 1. Other outputs may be indicative of the detected condition and are also within the scope of these inventions.

Further, the sensor may monitor flow development along assay 21 to assess whether an inadequate sample volume has been applied to assay 21, or that excess volume has been applied. For instance, prior to determining the test result, the sensor may monitor the flow progress on assay 21 along flow line 44. In other examples, the sensor will monitor flow progress at both flow line 44 and along the assay, for instance at intermediary flow line 46. The sensor may be configured to sense whether an adequate flow of a reagent occurred on assay 21, while assay 21 was within cavity 3, and/or whether one or more lines, i.e. reflectance or transmission values, were present on assay 21 prior to contact of assay 21 with the sample to be tested.

In addition, the sensor may be configured to detect whether dirt/debris is contaminating the optical path. For instance, the sensor may monitor the optical path for interference such as by debris. To determine that a test has run properly, or that the assay is free of dirt/debris, predetermined optical measurements, such as reflectance values or transmission values, may be stored electronically. The preset values, or preset parameters, can include a theoretical reflectance, or transmission, value from an unused assay (prior to receiving reagents). Preset values may also include values may be one or more theoretical test lines and/or one more theoretical control lines on the assay, and may also include a difference between the theoretical reflectance values for the one or more control lines and the theoretical value for the one or more test lines.

Figure 13:
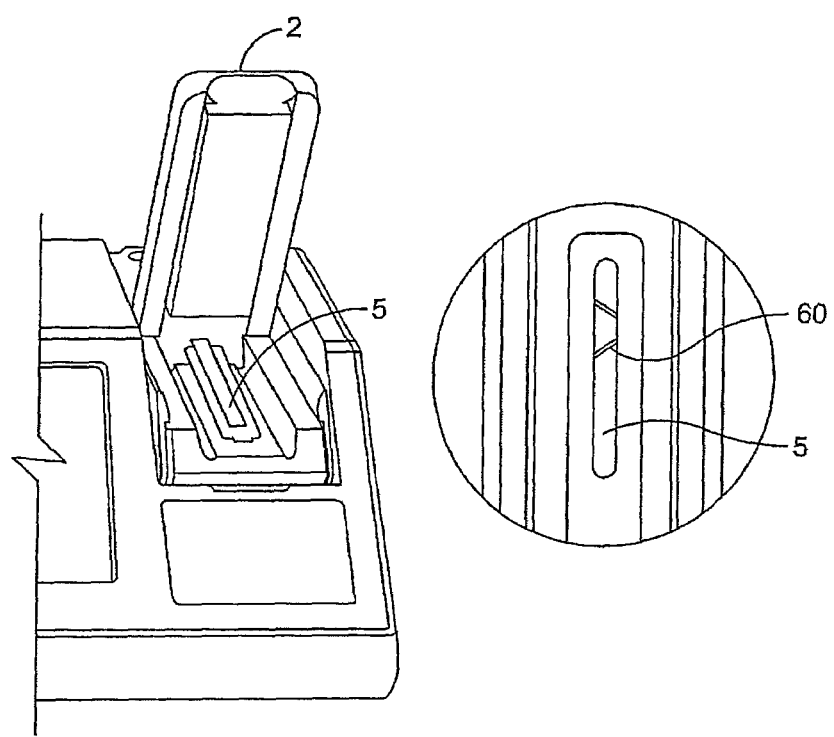
FIG. 13 is a front perspective view of one embodiment of a lateral flow assay system with debris on the imaging detector.

FIG. 13 shows one embodiment of lateral assay system 1, with debris 60 over light aperture 5. In use, a reflectance value on an assay that is inconsistent with the theoretical reflectance value may indicate a contaminated optical path, such as debris 60 as shown here. Lateral assay system 1 may be adapted to generate a no-run response and/or deactivate reader 100 and/or incubator 102 when the sensor detects such an aberration.

In other examples, the optical detector may monitor at least one pre-test parameter after the optical detector has already acquired at least one image detection on the assay. Similarly, optical detector generates a test result from assay 21, for instance by a comparison between at least two lines on the assay, for examples lines 40 and 42 of the test strip depicted in FIG. 7. As indicated above and in the incorporated references, optical detector may compare changes in reflectance values of two lines on the assay, for instance at least one test line 40 and at least one control line 42.

Particular embodiments include configuring the lateral flow assay system to allow concurrent incubation and reading of assay 21. The combination allows sensors to be used to detect not only test results, but also to check parameters that might indicate whether or not flow has occurred on the assay and that such flow caused a proper test result. That is, while sample, including the potential analyte, or analytes, of interest, is flowing on assay 21 and binding is occurring in a mobile phase and on assay 21, the assay is being incubated. By combining reader 100 and incubator 102 into such an integral diagnostic unit 1, results can be achieved quicker than when assays, such as test strips or other test medium, are incubated in one device and then moved to a separate device for reading. For instance, speed-to-result can be enhanced, for example to as little as less than about 60 seconds or even less than about 30 seconds. Generally, such a combined system can be dynamic, sensing changes in the assay as they occur by looking for areas of decreased reflectance and/or transmission anywhere on the unused or not-fully developed assay.

A level of protection is provided to prevent pre-run assays from being read (for example, reader 100 will determine if line development, for instance at flow line 44, intermediary flow line 44, test line 40 and/or control line 42 occurred prior to the time when sample flow could have reached such line) and to prevent incorrect readings caused by debris, or similar interference with system optics.

Various triggers may initiate assay analysis of system 1. For example, closing of hood 2 may initiate test operation, including optical measurement. Alternatively a separate switch can be used to initiate test operation after hood 2 is closed. In either case, a first reading may determine whether a proper assay is correctly position in the system. If assay 21 is detected, a reading sequence is initiated. For example, optical measurement, such as to detect light reflected off assay 21, can utilize values, such as average reflectance values, in certain areas of assay 21. Initially system 1 may analyze the assay to determine if the optical path is clear of interference, such as from debris. Debris can be in any number of locations in the optical path including on assay 21 or assay container 22. Concurrently with analyzing the optical path for debris, or subsequent thereto, the system can analyze the assay to determine if line development has already occurred. That is, whether a proper assay has been inserted into cavity 3. For example, test strips configured to develop within certain areas, such as a test line and control line, should have no development in those areas before the analyte and mobile phase have had adequate time to reach them.

In some examples, lines configured to develop a change in reflectance, and/or transmission, when contacted by reagents and sample should not develop until flow of sample and reagents has arrived and binding has occurred. That flow will not have arrived at the time of an initial, for example about three second, read. As such, if line development is detected at the initial assay analysis, then an error message will be delivered to the user and further readings, for example further optical measurements, can be aborted. In this way, this mechanism can detect the use of pre-run (known negative) assay or pre-marked assays. Generally, when reflectance is reduced on an unused assay, either by the presence of line development or other darkening of the assay away from baseline, the reduction in reflectance can inform the user that something has occurred either on the assay or in the optical path, so that the result should not be accepted.

After initial optical readings are found satisfactory and appropriate reader parameters and incubator temperatures are selected, either manually or automatically, further optical readings, for example approximately fifteen seconds after sample has been applied, can be used to determine whether adequate flow has occurred. For example, optical readings can determine whether or not reagents have flowed between a sample application region and a downstream line such as a test line.

The presence of label, such as colored particles, for example gold sol beads, flowing in the mobile phase, and the resulting reflectance changes on the assay between the sample application area and a first test line, can inform the user that flow is occurring and return an error message if no flow is detected. An assay lacking predictable reflectance changes might either have had no sample flow, or inadequate sample flow. Certain measurements can also indicate whether excessive flow has occurred, as in the case where too great a volume of sample has been applied to a test strip and possible reflectance change due to reagents is overwhelmed by the excessive sample volume. Reflectance changes between the sample application area and result detection areas, such as test line and control line, can be temporary and disappear as the mobile phase flows. If optical measurements are taken such temporary/non-permanent changes can be detected.

If an assay, including a test strip or other assay type, has passed the preliminary readings, system 1 may initiate readings to generate a test result. For example, after approximately thirty seconds test line and control line analysis can begin. When there is enough differentiation, for example percent reflectance difference, between the test and control, a result can be provided. Typically, negative results and more extreme results can be provided sooner and results closer to threshold levels will take longer. For example, in the case of a test in which the reflectance value on the test line relates inversely to the amount of analyte, if the test line reflectance is reduced to a certain level then a negative result can be called. In some examples, if hood 2 is opened while reader 100 is reading the assay, a signal may generate a no-result response.

Reader 100 and/or incubator 102 may be powered by a power source. In some examples for on-site analysis, for instance in rugged environments, the power source may be a vehicle battery. Further, reader 100 may be in communication with an onboard vehicle system.

As introduced in FIG. 14, lateral flow assay system 1 may include removable assay module 104 to be removed from system 1 and cleaned from debris. Typically, removable assay module 104 includes a similar assay cavity as described above, to align assay 21 with optics of reader 100 while in a closed testing position. In some examples, the assay is a lateral flow test strip and the assay cavity within removable assay module 104 is sized to receive the lateral flow test strip.

As discussed above, removable assay module 104 may include a hood. The hood may enclose the assay in a closed testing position and be opened to clean away debris in an open maintenance position when removable assay module 104 is removed from system 1. In some examples, if the hood of removable assay module 104 is opened while reader 100 is reading the assay, a signal may generate a no-result response. Further, removable assay module 104 may have a bottom face having a window 108 to slide in between reader 100 and the assay in a manner so that at least one light aperture 5 aligns with the assay in a closed testing position. Window 108 may be removable and cleanable as discussed above, and further the bottom face may include holes to receive an adjustment fastener to secure removable assay module 104 into an optical alignment with reader 100. In other examples, bottom face 108 may include engagement lip 106 to position bottom face 108 securely with reader 100.

Figure 15:
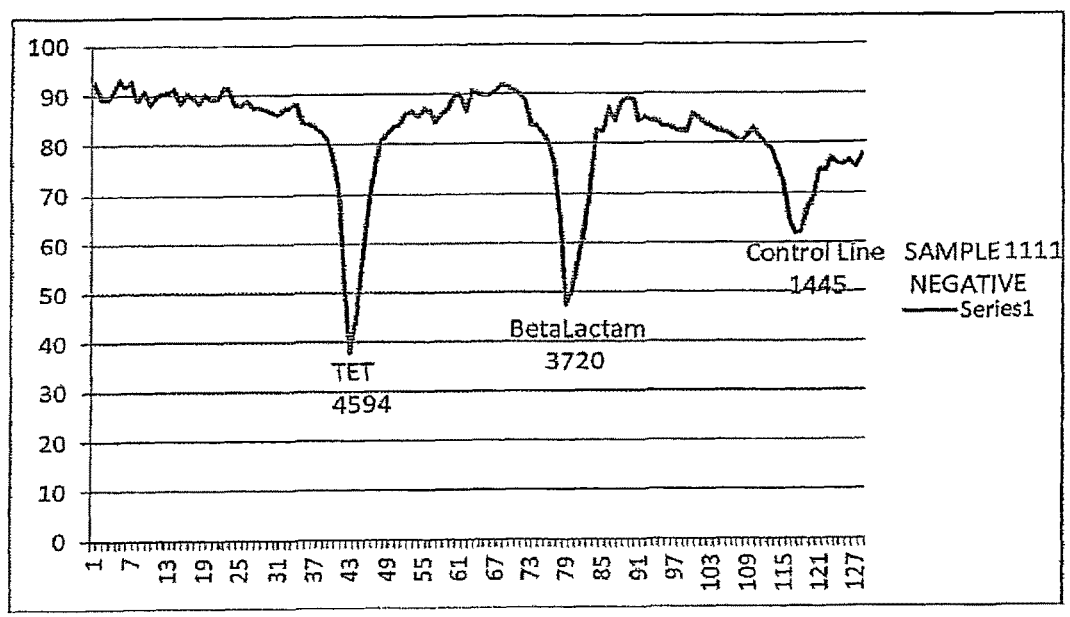
FIG. 15 is an example of a graphical assessment of a negative diagnostic development of one embodiment of a lateral flow assay system.
Figure 16:
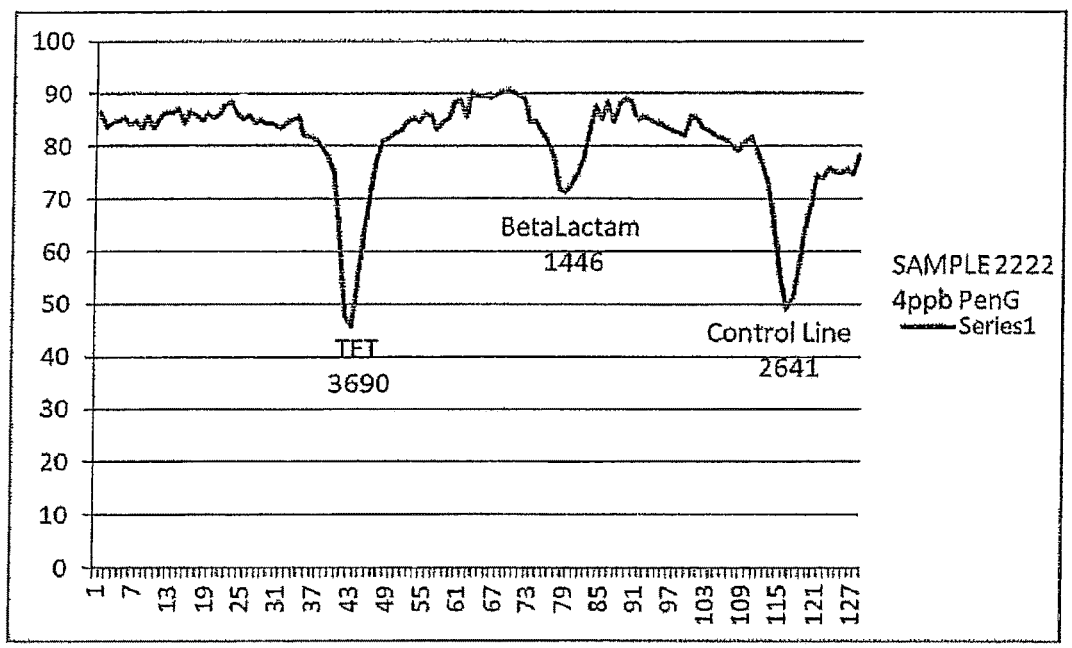
FIG. 16 is an example of a graphical assessment of both a negative result for one analyte and a positive result for a second analyte embodiment of a lateral flow assay system.
Figure 17:
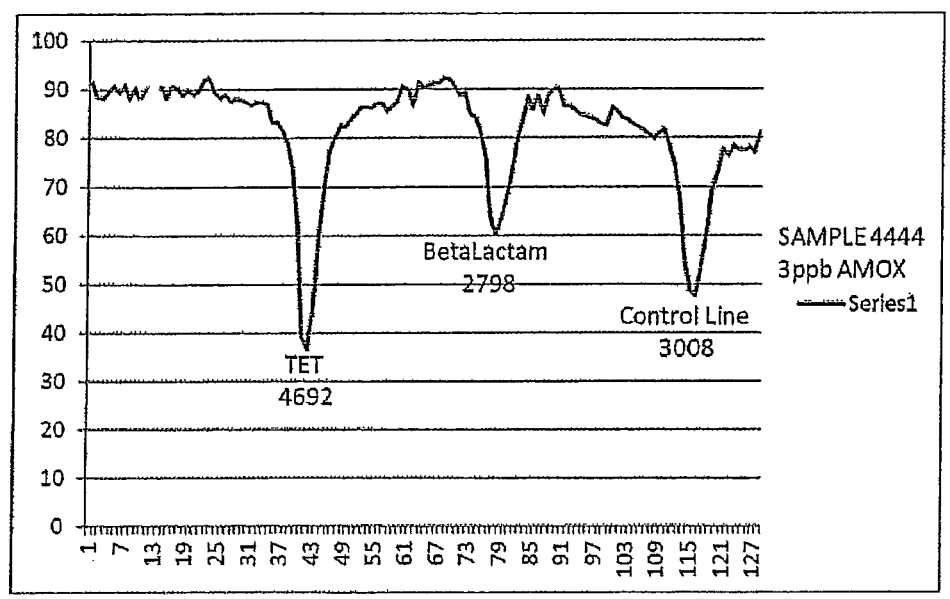
FIG. 17 is a yet another example of a graphical assessment of both a positive result for one analyte and a negative result for a second analyte embodiment of a lateral flow assay system.

FIGS. 15-17 include examples of results from testing for the detection of multiple analytes. As shown, these graphs display the assay analysis development during the detection of beta-lactam and tetracycline using two test lines 40 and one control line 42. These graphs therefore illustrate three test development lines. A graph for the detection of a single analyte would typically include two lines: a test line and control line.

In some examples, the y-axis of the graphs is a measurement of reflectance and the x-axis is the remission value. Remission may be the reflection or scattering of light by a material discussed herein on the assay (i.e. lateral flow strip). Typically, test line development results in decreased reflectance on an assay and, therefore, line development is shown as a reverse peak. In particular embodiments, the assay (i.e. lateral flow strip) area is broken into 128 remission values. For instance, the numbers of the x-axis reflect a reading of each of the 128 values which are in a 1×128 matrix on the assay (i.e. lateral flow strip). Therefore, flow of the sample may be sequential from 1 to 128 along the assay. Other examples of graphical displays include a variety of test result measurements.

FIG. 15 depicts one example of results from a negative sample. As graphically represented, both the tetracycline and beta-lactam line development show greater reflectance reduction (i.e. greater line intensity) than the control line.

FIG. 16 shows one example of a negative result for tetracycline and a positive result for the beta-lactam penicillin G. Here, the tetracycline line intensity is greater than the control line, and the beta-lactam line intensity is less than the control line, for instance due to inhibition of the beta-lactam binder by penicillin G from the sample.

FIG. 17 illustrates another example of a negative result for tetracycline and positive result for the beta-lactam amoxicillin. Here, the tetracycline line intensity is greater than the control line and the beta-lactam line intensity is less than the control line, for instance due to inhibition of the beta-lactam binder by amoxicillin from the sample.

Figure 18:
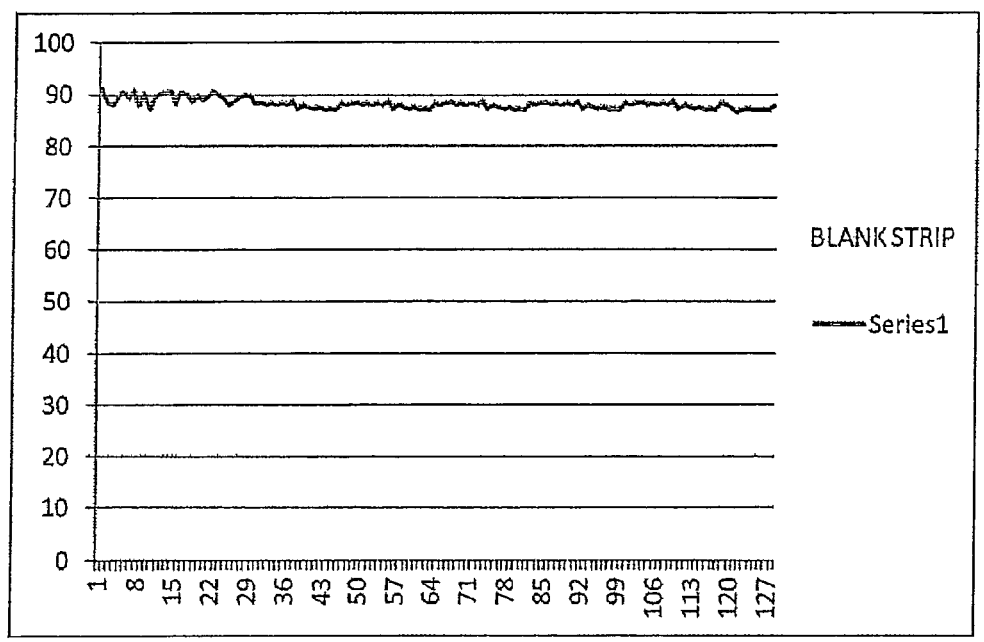
FIG. 18 is an example of a graphical assessment of a baseline diagnostic development of a blank assay.

FIG. 18 shows a graphical assessment of a baseline diagnostic development of a blank assay embodiment, for example illustrating analysis development of a blank strip (i.e. a strip upon which no sample development has occurred).

Figure 19:
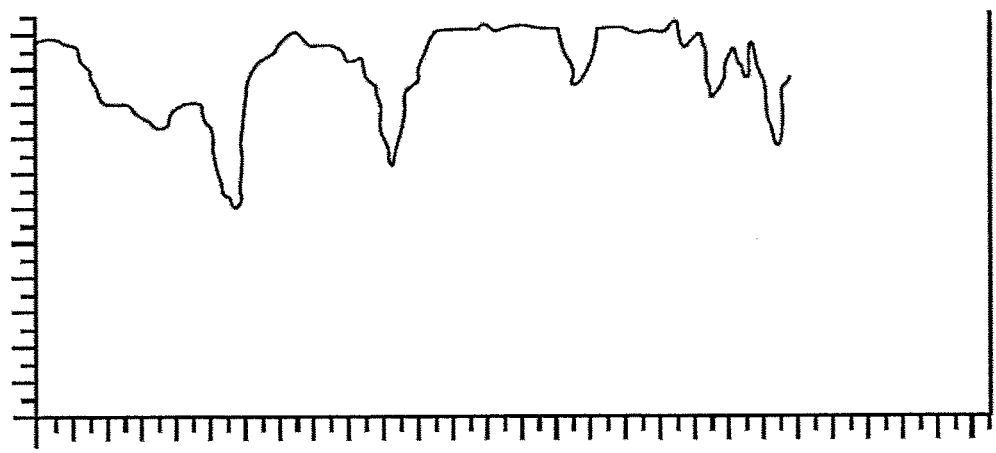
FIG. 19 illustrates one embodiment of a user interface with a graphical representation of the diagnostic test development from an assay.

FIG. 19 illustrates one embodiment of the user interface having a graphical representation of the diagnostic test development from an assay on the display board. Other embodiments of user interface includes multiple sizes and remote access display boards, for instance to allow the user to better assess and monitor the development of test results.

In other embodiments, the disclosure includes a lateral flow assay system 1 kit. In this embodiment, the kit may comprise an incubator, e.g. any of the incubators and/or incubator components previously shown or described, and a reader, e.g. any of the readers and/or reader components shown or described.

In yet another embodiment of the disclosure, a method for analyte analysis includes incubating the assay, e.g. including any of the embodiments previously shown or described, and reading the assay to generate a test result, e.g. including any of the embodiments previously shown or described. In particular examples, a diagnostic test method for detecting an analyte in a test sample includes adding a test sample to a test medium, such as a lateral flow test strip, to create an assay, the test medium configured to provide a detectable test result after incubation with the test sample; enclosing the test medium within a hood, the hood configured to enclose a cavity, the cavity configured to receive the test medium and connected with a temperature control source, the temperature control source capable of maintaining a consistent temperature; positioning a sensor, such as an optical sensor capable of reading reflectance from the test medium, relative to the test medium so that a change on the test medium is detectable by the sensor; and activating the sensor, such as by closing the hood, the activation causing the sensor to compare the test medium to a preset parameter. When the test medium is not within the preset parameter, a test result is not provided, and wherein when the test medium is within the preset parameter, the test result is determined from the test medium, the test result indicating whether an analyte was detected in the test sample.

In other embodiments of the methods, a preset parameter can be used to determine either or both whether an adequate flow of reagents occurred on the test strip while the test strip was within the cavity and whether one or more test lines are present on the test strip prior to being contacted by the test sample. To do so the sensor can be configured to continuously analyze changes on the test medium until a test result occurs. The test result can be determined by a comparison between changes, such as reflectance changes, in a first line, for example a test line, and a second line, for example a control line, on the test strip.

A further example of the methods include using preset parameters to compare the test strip, prior to sample flow thereon, including prior to sample application, with the actual strip being used. For example, a blank strip, prior to reagent flow or prior to sample application, will have a theoretical reflectance profile within a predictable range. If areas of reduced reflectance are detected, that did not result from sample/reagent flow on the strip, then it is possible not only that something untoward has occurred with the test strip but also it is possible that the optical path has become contaminated and requires cleaning. Such contamination can be on the strip or within the reader. Generally, an unused test strip should have no areas of reduced reflectance. Any such areas can indicate a problem, whether from dirt/debris, use of a test strip that was already run, or otherwise. In any case, the test result may not be valid.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

What is claimed is:

1. A lateral flow assay system to generate a diagnostic test development from an assay, said system comprising:
   a. an incubator configured to incubate said lateral flow assay;
   b. a reader configured to detect a first transmission of light on said assay in a stationary imaging position while also being configured to detect at least a subsequent transmission of light on said assay in said stationary imaging position as said system synchronizes said incubator incubating said assay to generate said test result; and
   c. a user interface having a graphical display of said diagnostic test development, said graphical display includes a first axis having a measurement of reflectance on said assay and a second axis having a measurement of a remission value of said assay, and whereby said reflectance measurement and said remission value graphically illustrate said diagnostic test development.

2. The apparatus of claim 1, wherein said graphical display includes a test result assessment about every fifteen seconds.

3. The apparatus of claim 1, wherein said graphical display includes at least one valley mirroring a line development on said assay.

4. The apparatus of claim 1, wherein said assessment includes a lowest reflectance point on said assay.

5. The apparatus of claim 1, wherein said user interface includes an integrated circuit board supporting a display board.

6. The apparatus of claim 5, wherein said display board includes a graphical display of said diagnostic development.

7. The apparatus of claim 1, wherein said assay is a lateral flow assay.

8. The apparatus of claim 7, wherein said assay is a lateral, capillary-flow, elongated test strip.

9. An assay measurement apparatus to generate a diagnostic test development from an assay, said apparatus comprising:
   a. an optical detector aligned in an optical path with said assay, wherein said optical detector is configured to acquire a first image detection on said assay in a stationary imaging position while also being configured to acquire at least a subsequent image detection on said assay in said stationary imaging position; and
   b. a microprocessor in electrical communication with said optical detector, wherein said microprocessor is programmed to signal said optical detector to synchronize image detection of said assay to generate a graphical display assessment of said diagnostic development.

10. The apparatus of claim 9, wherein said graphical display illustrates a measurement of reflectance on said assay and a measurement of a remission value on said assay.

11. The apparatus of claim 10, wherein said graphical display includes a test result assessment about every fifteen seconds.

12. The apparatus of claim 10, wherein said graphical display includes at least one valley mirroring a line development on said assay.

13. The apparatus of claim 9, wherein said assessment includes a lowest reflectance point on said assay.

14. The apparatus of claim 10, wherein said apparatus includes a user interface.

15. The apparatus of claim 14, wherein said user interface includes an integrated circuit board supporting a display board.

16. The apparatus of claim 15, wherein said display board includes a graphical display of said diagnostic development.

17. The apparatus of claim 9, wherein said assay is a lateral flow assay.

18. The apparatus of claim 17, wherein said assay is a lateral, capillary-flow, elongated test strip.

19. A method of assessing diagnostic test development from an assay, the method comprising:
   a. aligning an optical detector in an optical path with said assay;
   b. acquiring a first image detection on said assay in a stationary imaging position and acquire at least a subsequent image detection on said assay in said stationary imaging position;
   c. signaling said optical detector to perform continuing image detection of said assay; and
   d. generating a graphical assessment of said continuing image detection of said diagnostic test development.

20. The method of claim 19, wherein generating said assessment includes graphing a reflectance detected from said assay on a display board.

\* \* \* \* \*

UNITED STATES PATENT AND TRADEMARK OFFICE
CERTIFICATE OF CORRECTION

PATENT NO. : 10,274,489 B2
APPLICATION NO. : 14/823321
DATED : April 30, 2019
INVENTOR(S) : Robert J. Markovsky et al.

Page 1 of 1

It is certified that error appears in the above-identified patent and that said Letters Patent is hereby corrected as shown below:

On the Title Page

Item (72) Inventors: --Robert J. Markovsky, Brentwood, NH (US); Richard T. Skifflington, North Reading, MA (US); Stanley E. Charm, Boston, MA (US)-- should read "Robert J. Markovsky, Brentwood, NH (US); Richard T. Skifflington, North Reading, MA (US); Stanley E. Charm, Boston, MA (US); Paul E. Graham, Dracut, MA (US)"

Signed and Sealed this
Seventeenth Day of May, 2022

Katherine Kelly Vidal
*Director of the United States Patent and Trademark Office*